United States Patent [19]

Gossett et al.

[11] Patent Number: 5,196,424

[45] Date of Patent: Mar. 23, 1993

[54] N-[2-AMINO-4-SUBSTITUTED[[(PYRROLLO OR PYRIDO)[2,3-D]PYRIMIDINYL]-ALKYL]-BENZOYL]-L-GLUTAMIC ACIDS

[75] Inventors: Lynn S. Gossett, Indianapolis; Chuan Shih, Carmel, both of Ind.

[73] Assignee: Eli Lilly and Company, Indianapolis, Ind.

[21] Appl. No.: 856,611

[22] Filed: Mar. 24, 1992

[51] Int. Cl.$^5$ .................. A61K 31/505; C07D 471/04; C07D 475/04; C07D 475/08
[52] U.S. Cl. ..................................... 514/258; 544/280
[58] Field of Search .................. 544/280; 514/258

[56] References Cited

U.S. PATENT DOCUMENTS

| | | | |
|---|---|---|---|
| 4,595,530 | 6/1986 | Nishimura et al. | 544/280 |
| 4,684,653 | 8/1987 | Taylor et al. | 514/258 |
| 4,882,333 | 11/1989 | Shih et al. | 514/258 |
| 4,902,796 | 2/1990 | Taylor et al. | 544/279 |
| 4,921,858 | 5/1990 | Malone et al. | 544/280 |
| 4,923,872 | 5/1990 | Kostlan et al. | 544/280 |
| 4,927,828 | 5/1990 | Taylor et al. | 514/258 |
| 4,976,206 | 2/1991 | Taylor et al. | 544/280 |
| 4,988,702 | 1/1991 | Kostlan et al. | 544/280 |
| 4,988,813 | 1/1991 | Taylor et al. | 544/279 |
| 5,026,851 | 6/1991 | Taylor et al. | 544/279 |

FOREIGN PATENT DOCUMENTS

| | | |
|---|---|---|
| 0334636 | 9/1989 | European Pat. Off. |
| 0340905 | 11/1989 | European Pat. Off. |
| 0434426 | 6/1991 | European Pat. Off. |

OTHER PUBLICATIONS

Taylor, et al., *J. Med. Chem.*, 28, 914–921 (1985).
Seela, et al., *Liebigs Ann. Chem.*, 15–19 (1987).
Bernetti, et al., *J. Org. Chem.*, 27, 2863–2865 (1962).
Temple, et al., *J. Org. Chem.*, 47, 761–763 (1982).
Taylor, et al., *J. Org. Chem.*, 48, 4852–4860 (1983).

*Primary Examiner*—Cecilia Tsang
*Attorney, Agent, or Firm*—Steven A. Fontana; Leroy Whitaker; John C. Demeter

[57] ABSTRACT

This invention relates to N-[2-amino-4-substituted-[[(pyrrolo or pyrido) [2,3-d]pyrimidinyl]-alkyl]benzoyl]-L-glutamic acid compounds, intermediates for their synthesis, pharmaceutical formulations containing those compounds, and their use as antineoplastic agents.

20 Claims, No Drawings

N-[2-AMINO-4-SUBSTITUTED[[(PYRROLLO OR PYRIDO)[2,3-D]PYRIMIDINYL]-ALKYL]BENZOYL]-L-GLUTAMIC ACIDS

BACKGROUND OF THE INVENTION

This invention relates to N-[2-amino-4-substituted-[[(pyrrolo or pyrido)[2,3-d]pyrimidinyl]-alkyl]benzoyl]-L-glutamic acid compounds, certain of their reduced forms, intermediates for their synthesis, pharmaceutical formulations containing those compounds, and their use as antineoplastic agents.

Folic acid is a coenzyme in various enzymatic reactions such as those in the biosynthesis of nucleic acid and the metabolism of amino acids and peptides. Folate cofactors which are derived from folic acid are essential to biosynthesis of nucleic acids in two pathway—the purine synthetic pathway and the thymidine synthetic pathway. Generally, folic acid is required to be transformed into its activated coenzyme form by a two step reduction before it becomes biologically active. Compounds such as amethopterin are known to inhibit the second reduction, from dihydrofolic acid to tetrahydrofolic acid, by coupling strongly with the required enzyme, dihydrofolic reducatase. Such inhibitors are continuously being developed as antitumor drugs because they may disturb the DNA synthesis and cause cell death by preventing the regeneration of biologically active tetrahydrofolates.

Various derivatives of folic acid and aminopterin have been synthesized and tested as folic acid metabolite inhibitors. Among these are various "deaza" compounds in which a methylene or methylidene group occupies a position in the molecule normally occupied by an imino or nitrilo group, respectively. These derivatives have varying degrees of activity as metabolite inhibitors. A tetrahydroaminopterin antitumor agent 5,10-dideaza-5,6,7,8-tetrahydroaminopterin (DDATHF) inhibits glycinamide ribonucleotide transformylase, an enzyme required in the initial stage of purine biosynthesis; J. Med. Chem., 28, 914 (1985).

In European Patent Application EP 0 334 636, certain pyrrolopyrimidine derivatives are disclosed as having antitumor effects in mammals. In U.S. Pat. No. 4,684,653 certain pyrido[2,3-d]pyrimidine derivatives are disclosed as antineoplastic agents. The compounds of the present invention are distinguished from the above two references at least by virtue of their 4-position substituent.

SUMMARY OF THE INVENTION

The present invention relates to compounds having the formula,

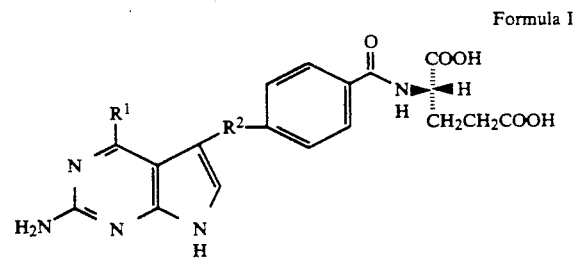

Formula I wherein:
$R^1$ is hydrogen, chloro, mercapto, $C_1$-$C_4$ alkylthio, $C_1$-$C_4$ alkoxy, $C_1$-$C_4$ alkylamino, or di($C_1$-$C_4$)alkylamino;
$R^2$ is a $C_2$-$C_3$ alkyl; and pharmaceutically acceptable salts thereof.

A further aspect of the present invention are compounds having the formula,

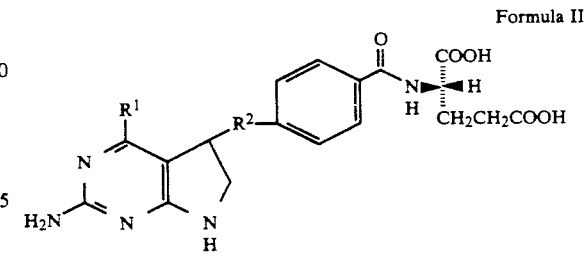

Formula II where $R^1$ and $R^2$ are as defined above for Formula I, and pharmaceutically acceptable salts thereof.

A further aspect of the present invention are compounds having the formula,

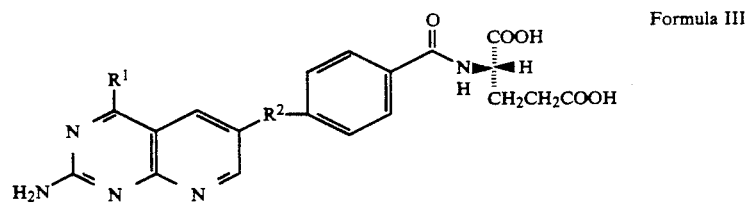

Formula III wherein:
$R^1$ is hydrogen, chloro, mercapto, $C_1$-$C_4$ alkylthio, $C_1$-$C_4$ alkoxy, $C_1$-$C_4$ alkylamino, or di($C_1$-$C_4$)alkylamino;
$R^2$ is $C_2$-$C_3$ alkyl; and pharmaceutically acceptable salts thereof.

A still further aspect of this invention are compounds of the formula,

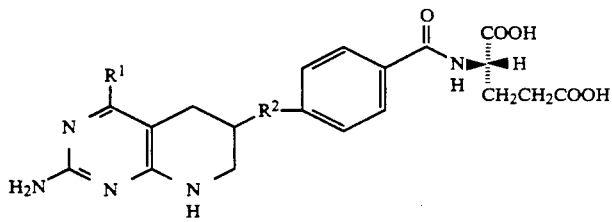

Formula IV where R[1] and R[2] are as defined above for Formula III, and pharmaceutically acceptable salts thereof.

The invention also relates to intermediates useful to prepare compounds of Formulae I, II, III, or IV; and to compositions and methods for the use of such compounds in combatting neoplastic growth.

DETAILED DESCRIPTION OF THE INVENTION

The present invention relates to compounds of Formulae, I, II, III, and IV and intermediates for their synthesis. These intermediates are those having the formulae

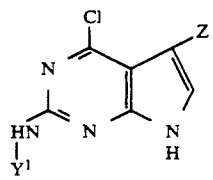

where $Y^1$ is hydrogen or an amino protecting group;

Z is hydrogen, bromo or iodo· and pharmaceutically acceptable salts thereof; and

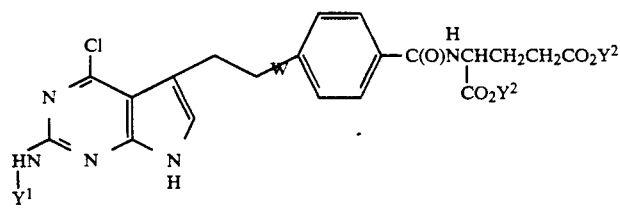

where:

W is a bond or —$CH_2$—;

$Y^1$ is an amino blocking group;

$Y^2$ is the same or different carboxy protecting group; and pharmaceutically acceptable salts thereof.

In Formulae I, II, III, and IV, the configuration of the L-glutamic acid residue is shown unambiguously. The glutamic acid residue for all compounds disclosed herein is in the L-configuration.

The term "$C_2$-$C_3$ alkyl" group means a straight chain divalent alkyl group having the stated number of carbon atoms such as 1,2-ethanediyl and 1,3-propanediyl.

The term "alkylthio" means a straight or branched chain alkyl group having 1 to 4 carbon atoms in length bonded to a thio group to afford a methylthio, ethylthio, propylthio, isopropylthio, n-butylthio, isobutylthio, sec-butylthio, or tert-butylthio radical.

The term "alkoxy" means a straight or branched chain alkyl group of 1 to 4 carbon atoms bonded to an oxo group to afford a methoxy, ethoxy, propoxy, iso-propoxy, n-butoxy, iso-butoxy, sec butoxy, or tert-butoxy radical.

The term "alkylamino" means an alkyl group of 1 to 4 carbon atoms bonded to an amino group to afford a methylamino, ethylamino, propylamino, isopropylamino, or butylamino radical.

The term "dialkylamino" means —$NR^3R^4$ where $R^3$ and $R^4$ are the same or different alkyl groups of 1 to 4 carbon atoms in length such as dimethylamino, diethylamino, diproylamino, diisopropylamino, dibutylamino, or methylethylamino.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are ($C_1$-$C_4$ alkyl)carbonyl and trimethylacetyl, and most preferred is trimethylacetyl. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used herein refers to one Of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4 -dimethoxybenzhydryl, 2,2',4,4'-tetramethoxybenzhydryl, methyl, ethyl, propyl, isopropyl, t-butyl, t-amyl, trityl, 4-methoxytrityl, 4,4'dimethoxytrityl, 4,4'4"-trimethoxytrityl, 2-phenylprop-2-yl,trimethylsilyl, t-butyldimethylsilyl, phenacyl, 2,2,2-tricholorethyl, β-(trimethylsilyl)ethyl, β-(di(n-butyl)methylsilyl-)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups. Preferred protecting groups are ethyl and propyl.

As mentioned above, the invention includes pharmaceutically acceptable salts of the compounds defined by the above formula. A particular compound of this invention can possess a sufficiently acidic, a sufficiently basic, or both functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4- dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate,and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from nontoxic inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

The preferred starting materials for preparing compounds of the present invention are 2-amino-4-oxopyrrolo[2,3-d]pyrimidine (Formula V, below) or 2-(tert-butoxycarbonyl)-amino-4-oxo-6-ethynyl-pyrido[2,3-d]pyrimidine (Formula VI, below); depending on whether the pyrrolo derivative or the pyrido derivative is the desired product.

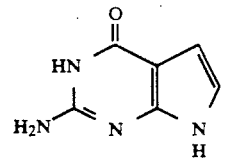

Formula V

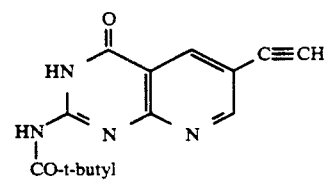

Formula VI

The compounds of the present invention, or their precursors, are prepared using procedures known to those of ordinary skill in the art. To the extent not commercially available, (such as 2-amino-4-oxo-pyrrolo[2,3-d]pyrimidine; also known as 7-deazaguanine available from Sigma Chemical Company), the pyrrolo compounds of the present invention can be prepared by conventional organic chemistry methods using commercially available reagents.

The 2-(trimethylacetyl)amino-4-oxo-5-ethynyl-pyrido[2,3-d]pyrimidine compound is prepared according to the procedures described in Taylor et al., J. Org. Chem., 54, 3618-3624 (1989) which is incorporated by reference herein.

The first step to synthesize the pyrrolo compounds of the present invention requires reacting a compound of Formula V with a chlorinating agent in the presence or absence of an inert or substantially inert solvent or mixture of solvents. The reaction is depicted below in Equation 1, Equation 1

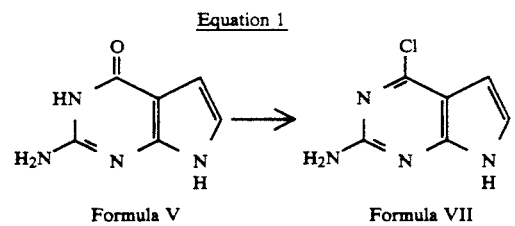

Formula V           Formula VII

Suitable chlorinating agents are any compound which releases chloride ions. Preferred chlorinating agents are POCl₃ and PCl₃.

Although this reaction can be carried out in the presence or absence of a solvent, preferably it is carried out neat.

The amount of chlorinating agent employed in this reaction is an amount sufficient to displace the 4-oxo group with a chloro group. Generally, from about one equivalent of chlorinating agent to an excess of chlorinating agent per equivalent of pyrrolo pyrimidine is employed. Preferably an excess of chlorinating agent is used.

The temperature employed in this step is sufficient to effect completion of the chlorination reaction. The temperature is generally from about room temperature to about reflux and preferably at reflux.

The length of time for the first step can be any that is required for the displacement reaction to occur. The reaction generally requires from about 2 to about 6 hours. The optimal reaction time can be determined by monitoring the progress of the reaction by conventional chromatographic techniques such as thin layer chromatography, high performance liquid chromatography, or column chromatography.

The second and third steps, respectively, in synthesizing the pyrrolo compounds of the present invention requires adding a protecting group to the 2-amino group, and then reacting the corresponding amino-protected compound with N-iodo(or bromo)succinimide. The reaction sequence is depicted in Equation 2, Equation 2

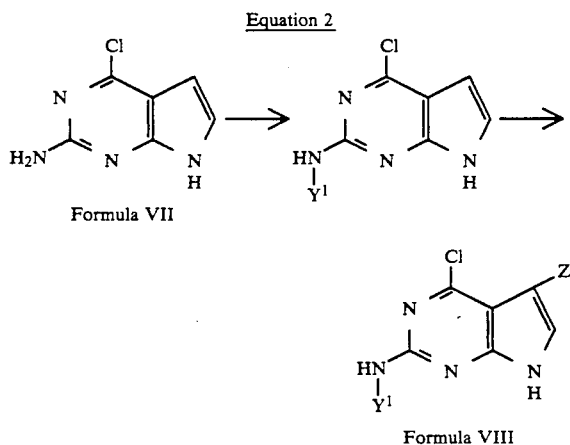

Formula VII

Formula VIII wherein:

Z is iodo or bromo; and $Y^1$ is an amino protecting group.

The addition of an amino protecting group is carried out under standard conditions for such a reaction known to those skilled in the art.

The halogen substituent is iodo or bromo, preferably iodo. Halogenation is accomplished by reacting the amino protected intermediate with N-iodosuccinimide or N-bromosuccinimide in the presence of a weak base in the presence or absence of an inert or substantially inert solvent or mixture of solvents, to afford the corresponding 5-halo intermediate.

Suitable bases for use in this reaction include tertiary amines such as triethylamine and pyridine. The preferred base is anhydrous pyridine.

Suitable solvents are generally polar high-boiling solvents such as dimethylforamide (DMF), glyme, tetrahydrofuran, (THF), and pyridine. The preferred solvent is anhydrous pyridine.

The amount of N-iodosuccinimide or N-bromosuccinimide employed in this reaction is generally an amount sufficient to react with all the amino-protected compound present. Typically equivalent amounts of reactants to a slight excess of N-iodosuccinimide or N-bromosuccinimide are used.

The temperatures employed are sufficient to affect completion of the halogenation reaction, and is preferably at about room temperature.

The length of time for the third step is that required for the halogention reaction to occur. The reaction requires a period of about 10 minutes to about 4 hours.

The optimal reaction time can be determined by monitoring the progress of the reaction by conventional chromatographic techniques, such as thin layer chromatography.

The fourth step to synthesize the compounds of the present invention is coupling the 5-halopyrrolo pyrimidine intermediate with a benzoic acid derivative. The process requires reacting an unsaturated compound having the formula

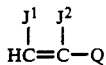

where $J^1$ and $J^2$ are both hydrogen or are taken together to form a carbon-carbon bond (i.e. an alkynyl group) and Q is a silyl protecting group preferably trimethylsilyl, with a 5-bromo or 5-iodo pyrrolo pyrimidine intermediate in the presence of a suitable solvent, a palladium catalyst, and preferably a secondary or tertiary amine. Analogous reactions are contained in Taylor et al. (U.S. Pat. No. 4,818,819) which is incorporated herein by reference.

The palladium catalyst used are those which have been employed previously in the reaction of aryl halides and allylic alcohols, as described for example by Melpoler et al., *J. Org. Chem.*, 41, 265, (1976); 265; Chalk et al., *J. Org. Chem.*, 41, 1206, (1976); Arai et al., *J. Heterocyclic Chem.*, 15, 351 (1978); Tamuru et al., *Tetrahedron Papers*, 10, 919 (1978); *Tetrehedron*, 35, 329 (1979).

Carboxy protecting groups are employed to protect the carboxylic acid groups on the benzoic acid derivative during the coupling reaction.

The coupling reaction is preferably conducted in the presence of at least one molar equivalent of a secondary or tertiary amine which acts as an acid acceptor, such as triethylamine or diethylamine.

Suitable solvents employed in this reaction preferably are anhydrous inert polar solvents such as acetonitrile, N,N-dimethylformamide, or N-methylpyrrolidone.

Moderately elevated temperatures, preferably from about 75° C. to about 125° C., and more preferably from about 85° C. to about 100° C., are employed.

The following alternative reactions utilize the palladium catalysts, and differ in whether the unsaturated compound is reacted with the pyrrolopyrimidine and then coupled to the benzoic acid derivative, or whether the unsaturated compound is reacted with the benzoic acid derivative and then coupled to the pyrrolopyrimidine. The unsaturated compounds include ethylene, acetylene, propene, or propyne.

In the first alternative, a pyrrolo[2,3-d]pyrimidine is reacted with an unsaturated compound. The intermediate afford by this reaction is desilylated using standard conditions for this reaction and then used as a reactant in the next reaction, which is the coupling reaction. These reactions are illustrated in the scheme below labelled Alternative 1.

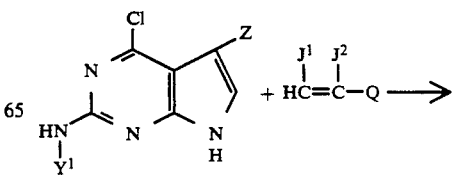

-continued corresponding unsaturated glutamate intermediate which is desilylated using standard conditions for this reaction and then coupled with a pyroolopyrimidine. These reactions are illustrated below in Alternative 2.

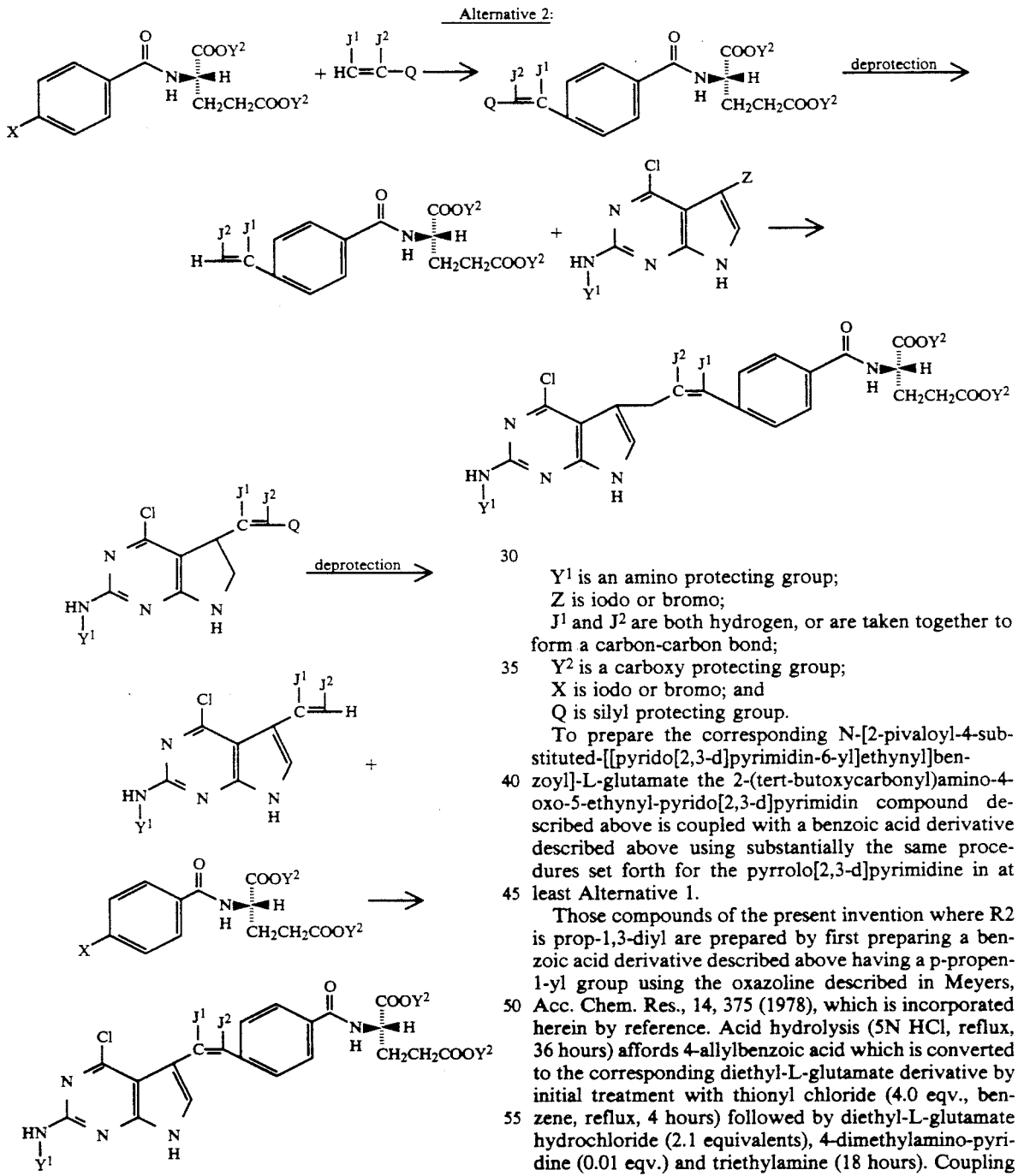

wherein:
Y¹ is a amino protecting group;
Y² is a carboxy protecting group;
Z is iodo or bromo;
J¹ and J² are both hydrogen, or are taken together to from a carbon-carbon bond;
Q is a silyl protecting group; and
X is iodo or bromo.

In the second alternative, the benzoic acid derivative is reacted with the unsaturated compound to form the Y¹ is an amino protecting group;
Z is iodo or bromo;
J¹ and J² are both hydrogen, or are taken together to form a carbon-carbon bond;
Y² is a carboxy protecting group;
X is iodo or bromo; and
Q is silyl protecting group.

To prepare the corresponding N-[2-pivaloyl-4-substituted-[[pyrido[2,3-d]pyrimidin-6-yl]ethynyl]benzoyl]-L-glutamate the 2-(tert-butoxycarbonyl)amino-4-oxo-5-ethynyl-pyrido[2,3-d]pyrimidin compound described above is coupled with a benzoic acid derivative described above using substantially the same procedures set forth for the pyrrolo[2,3-d]pyrimidine in at least Alternative 1.

Those compounds of the present invention where R2 is prop-1,3-diyl are prepared by first preparing a benzoic acid derivative described above having a p-propen-1-yl group using the oxazoline described in Meyers, Acc. Chem. Res., 14, 375 (1978), which is incorporated herein by reference. Acid hydrolysis (5N HCl, reflux, 36 hours) affords 4-allylbenzoic acid which is converted to the corresponding diethyl-L-glutamate derivative by initial treatment with thionyl chloride (4.0 eqv., benzene, reflux, 4 hours) followed by diethyl-L-glutamate hydrochloride (2.1 equivalents), 4-dimethylamino-pyridine (0.01 eqv.) and triethylamine (18 hours). Coupling to either the pyrrolo- or pyrido[2,3-d]pyrimidine, at least by Alternative 2, affords the compounds of the present invention where R² is a propen-1,3-diyl.

The fifth step to prepare the compounds of the present invention involves hydrogenating the compound of Formula IX in a suitable solvent in the presence of a catalyst. This step affords the corresponding 2-protected amino-4-chloro-[pyrrolo or pyrido(2,3-d)-pyrimidinyl]alkyl]-benzoyl]-protected L-glutamic acid of Formula X. The reaction is depicted in Equation 6, Equation 6

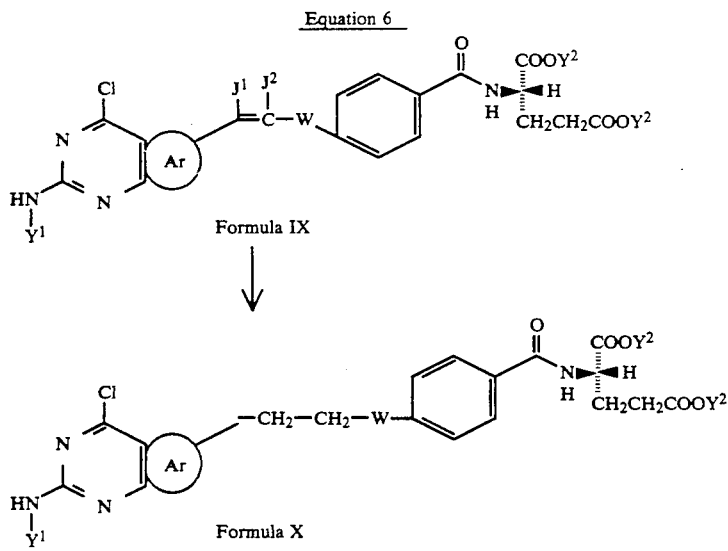

wherein:
Ar is pyrrolo or pyrido;
$Y^1$ is an amino protecting group;
$J^1$ or $J^2$ are both hydrogen or are taken together to form a carbon-carbon bond;
W is a bond or $CH_2$; and
$Y^2$ is a carboxy protecting group.

The solvent which is employed in the fifth step can be any solvent which will remain inert under the hydrogenation conditions. Suitable solvents include alcohols such as methanol, ethanol, 1-propanol, and 2-propanol. The most preferred solvent is ethanol.

The hydrogenation catalyst can be any material which contains a noble metal and will catalyze the reduction of the carbon bridge. Examples of suitable catalysts include noble metals supported on alkaline earth carbonates. Noble metals herein refer to gold, silver, platinum, palladium, iridium, rhodium, mercury, ruthenium and osmium. Preferred catalysts include palladium-on-carbon, platinum-on-carbon and platinum oxide. The most preferred hydrogenation catalyst is palladium on carbon.

The temperature and pressure employed in this step are those sufficient to effect completion of the hydrogenation reaction. Preferably from about 30° C., to about 150° C., most preferably from about 30° C., to about 75° C. Pressures employed are from about 1000 psi to about 1 psi, more preferably from about 400 psi to about 2 psi.

The present invention includes alternative 4-position atoms and groups, selected from hydrogen, mercapto, alkylthio, alkoxy, alkylamino, and dialkylamino groups. Chloro replacement by all, except hydrogen, can occur after the first step (Equation 1) after the third step (Equation 2) or after the fourth step (Alternative 1 and 2 coupling reactions) but before the protective groups removed, ($Y^1$ and $Y^2$). Hydrogen displacement of chloro can occur after the fourth step is performed or after the protective groups are removed (the sixth step, below).

The optimal reaction times for the above process steps can be determined by monitoring the progress of the reaction by conventional chromatographic techniques (such as thin layer chromatography, high performance liquid chromatography, or column chromatography), spectroscopic techniques (such as infrared spectroscopy, nuclear magnetic resonance spectrometry or mass spectrometry), or a combination of the two techniques.

Further descriptions of the various 4-position substituents of this invention follow:

4-Hydro Group

Displacement of the 4-chloro to afford the 4-hydro compound of the present invention is accomplished by continuing the hydrogenation of step five for a longer time period; past the point where the carbon bridge is saturated.

4-Mercapto or 4-Alkylthio Group

Displacement of the 4-chloro to form the corresponding mercapto or alkylthio compound of the present invention is accomplished by reacting the product of the first, third, or fifth step of this invention (compound of the Formula VII, VIII, or X) with a thiourea or dialkyldisulfide in the presence of a suitable solvent. Such chloro substitution reactions are known to those skilled in the art as exemplified by March, Advanced Organic Chemistry: Reactions, Mechanisms, and Structure, McGraw-Hill, 1st ed., p.500; which is incorporated herein by reference.

The solvent which is employed in this step can be any solvent which will remain inert under the reaction conditions. The preferred solvent is 2-methoxyethanol.

4-Alkoxy Group

Displacement of the 4-chloro to form the corresponding alkoxy compounds of the present invention is accomplished by reacting one of the compounds of Formula VII, VIII, or X of this invention with a nucleophile that releases the alkoxide ion, $R^3O^-$ in the presence of a suitable solvent. Such release can be accomplished by reacting the corresponding $C_1$-$C_4$ alkyl alcohol with an active metal such as sodium or magnesium to obtain the required alkoxide ion. For example:

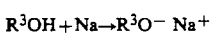

$$R^3OH + Na \rightarrow R^3O^- \; Na^+$$

Once the alkoxide ions are available, the Williamson synthesis involving the nucleophilic substitution of the alkoxide ion for the 4-chloro is used.

The solvent which is employed in this step can be any solvent which will remain inert under the reaction conditions. The preferred solvent is 2-methoxyethanol.

4-Alkylamino, or 4-Dialkylamino Groups

Displacement of the 4-chloro to form the alkylamino or dialkylamino moiety of the present invention is accomplished by reacting the intermediate of the first, third, or fifth step of this invention (compound of Formula VII, VIII, or X) with the corresponding nucleophilic alkylamine or dialkylamine in the presence of a suitable solvent. Similar chloro substitution reactions are known to those skilled in the art of orgainic chemistry as exemplified by March, Advanced Organic Chemistry: Reactions, Mechanisms, and Structure, McGraw-Hill, 1st ed.,p.502: which is incorporated herein by reference.

The solvent which is employed in this step can be any solvent which will remain inert under the reaction conditions. The preferred solvent is 2-methoxyethanol.

The sixth step of the present invention involves removing the protective groups, $Y^1$ and $Y^2$, from the compound of Formula X using basic hydrolysis. This process yields 2-amino-4-substituted-[[pyrrolo or pyrido(2,3-d)-pyrimidinyl]alkyl]benzoyl]-L-glutamic acid of Formula I or Formula III. Methods of removing the various protective groups are described in the standard references noted previously which are incorporated herein by reference.

An optional seventh step of the present invention involves catalytic hydrogenation of the compounds of Formula I or Formula III. The hydrogenation process yields the (pyrrolo or pyrido)pyrimidin compounds of Formula II or Formula IV.

The compounds employed as initial starting materials in the synthesis of the compounds of this invention are well known and, to the extent not commercially available, are readily synthesized by standard procedures commonly employed by those of ordinary skill in the art.

The pharmaceutically acceptable salts of the invention are typically formed by reacting a compound of this invention which possesses suitable acidic or basic functionality with an equimolar or excess amount of acid or base. The reactants are generally combined in a mutual solvent such as diethyl ether or benzene, for acid addition salts, or water or alcohols for base addition salts, and the salt normally precipitates out of solution within about one hour to 10 days, and can be isolated by filtration or other conventional means.

In addition, some of the compounds of the present invention may form solvates with water or common organic solvents. Such solvates are included as compounds of this invention.

The compounds of this invention have an inhibitory effect on one or more enzymes which utilize folate, and in particular metabolic derivatives of folate, as a substrate. For example the following representative compounds demonstrate inhibitory effects against growth of human T-cell derived lyphoblastic leukemia cells (CCRF-CEM):

Example 1, N-[2-amino-4-chloro-[[pyrrolo[2,3-d]-pyrimidin-5-yl]-ethyl]benzoyl]-L-glutamic acid Example 2, N-[2-amino-4-mercapto[[pyrrolo[2,3-d]-pyrimidin-5-yl]-ethyl]benzoyl]-L-glutamic acid Example 3, N-[2-amino-[[pyrrolo[2,3-d]-pyrimidin-5-yl]-ethyl]benzoyl]-L-glutamic acid Example 4, N-[2-amino-[di-hydropyrrolo[2,3-d]pyrimidin-5-yl]-ethyl]benzoyl-L-glutamic acid Example 5, N-[2-amino-4-methoxy[[pyrrolo[2,3-d]-pyrimidin-5-yl]-ethyl]benzoyl]-L-glutamic acid Example 6, N-[2-amino-4-diethylamino-[[pyrrolo[2,3-d]-pyrimidin-5-yl]-ethyl]benzoyl]-L-glutamic acid Example 7, N-[2-amino-[[tetrahydropyrido[2,3-d]-pyrimidin-6-yl]-ethyl]benzoyl]-L-glutamic acid The in vitro data reported in Table I was obtained using CCRF-CEM cells, a human leukemia cell line, (Foley et al., Cancer, 18, 522 (1965)) that were grown as previously described (Grindey, et al., J. Mol. Pharmacol., 16, 601, (1979)) both references incorporated herein by reference. Dose-response curves were generated for various compounds to determine the concentration required for 50% inhibition of growth ($IC_{50}$). Cluster plates were prepared in duplicate with the compound at various concentrations ranging from 100 $\mu g/ml$ to 0.005 $\mu g/ml$. Test compounds were dissolved initially in DMSO and further diluted with solvent to the desired concentration. Cells in Roswell Park Memorial Institute 1640 media supplemented with 10% dialyzed fetal bovine serum, and 16 mM HEPES buffer and 8mM MOPS buffer were added to the well at a final concentration of $4.8 \times 10^4$ cells/well in a total volume of 2.0 mL. After 72 h of incubation (95% air, 5% $CO_2$), cell numbers were determined on a ZBI Coulter counter. Cell number for indicated controls at the end of incubation was usually (4-6) $\times 10^5$ cells/well.

TABLE I

| Compound | $IC_{50}$ ($\mu g/ml$) |
| --- | --- |
| 1 | >20 |
| 2 | 0.032 |
| 3 | 0.019 |
| 4 | 0.005 |
| 5 | >2 |
| 6 | 0.9 |
| 7 | 0.005 |

The compounds of the present invention have been shown to be active against transplanted mouse tumors in vivo. The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Massachusetts). First passage tumor was stored in liquid nitrogen using standard techniques. The transplanted tumor was reestablished from the Tumor Bank every six months or as needed. The tumor was maintained by serial passage twice weekly in C3H mice.

In the procedure, the tumor was removed from passage animals and minced into 1- to 3-mm square fragments using sterile techniques. Tumor pieces were checked for sterility using both Antibiotic Medium 1 and Brain Heart Infusion (Difco, Detroit, Mich.). Recipient mice were shaved and tumor pieces were implanted subcutaneiously in the auxiliary region by trocar. Drug therapy on the appropriate schedule was initiated on the day after tumor implant. The compound being tested was mixed with 2.5 weight % of a polyoxyethylated oil known as "Emulphor EL 620" surfactant from GAF Chemicals Corporation (1:40 dilution of Empulphor in saline). All animals were weighed at the beginning and end of administration of the subject compounds. Food and water were provided ad libitum. The drug was administered in 0.5 ml of 2.5% Emulphor. Unless otherwise indicated, the compound was administered once per day for eight days. The tumor was measured the day after treatment ended with two dimensional measurements (width and length) of the tumor taken using digital electronic calipers interfaced to a microcomputer, J. F. Worzalla, et al., *Investigational New Drugs*, 8, 241-251 (1990). Tumor weights were calculated from these measurements using the following formula:

(tumor weight in mg) = width in mm)$^2$ × (length in mm)/2

At least one control group of an equal number of mice was treated with the same volume of 2.5% Emulphor only. The percent inhibition was calculated by substracting the ratio of the mean tumor size of the test group relative to the control group from 1 and multiplying the result by 100.

TABLE II

| Tumor System | Example 4 Results | | |
|---|---|---|---|
| | Dose Level (mg/kg) | % INH | Toxic/Total |
| 6C3HED | 50 | TOX | 10/10 |
| Lymphosarcoma | 25 | TOX | 10/10 |
| (Dailyx8) | 12.5 | 100 | 8/10 |
| | 6.25 | 100 | 6/10 |
| | 4.00 | 100 | 1/10 |
| | 2.00 | 97 | 0/10 |
| | 1.00 | 36 | 0/10 |
| | 0.50 | 1 | 0/10 |
| | 0.25 | 0 | 0/10 |
| 6C3HED | 16 | 100 | 0/10 |
| Lymphosarcoma | 8 | 100 | 0/10 |
| (Days 1,3,5,7) | 4 | 99 | 0/10 |
| | 2 | 49 | 0/10 |
| C3H Mammary | 32 | 95 | 9/10 |
| Adenocarcinoma | 16 | 92 | 6/10 |
| (Days 1,3,5,7,9) | 8 | 77 | 0/10 |
| | 4 | 24 | 0/10 |
| | 2 | 10 | 0/10 |
| | 1 | 0 | 0/10 |

The compounds of the present invention have also been shown to be active against isolated human dihydrofolate reductase (DHFR). Purified human dihydrogolate reductase was obtained from human leukemic lymphoblasts (WI-L2/M4 cells) according to the procedures described in Delcamp, T. J. et al., *Biochemistry*, 22, 633-639 (1983) which is incorporated herein by reference. Dihydrofolate reductase inhibition evaluations were carried out according to the procedures described in Rosowsky, A. et al., *Biochem. Pharmacol*, 35, 3327-3333 (1986) which is incorporated herein by reference. Dose response curves were generated for various compounds to determine the concentration required for 50% inhibition of enzyme activity (IC$_{50}$). The results of this evaluation are shown below in Table III.

TABLE III

| Compound | DHFR (5 × 10$^{-8}$ M) IC$_{50}$ |
|---|---|
| Example 4 | 9.6 × 10$^{-8}$ M |
| Example 7 | 6.4 × 10$^{-8}$ M |

The compounds of the present invention are antineoplastic agents and the invention provides a method of treating susceptible neoplasms in mammals, particulary humans. The method comprises administering a compound in the form of a pharmaceutical composition. The present compounds are useful in inhibiting the growth of neoplasms including choriocarcinoma, leukemia, adenocarcinoma of the female breast, epidermid cancers of the head and neck, squamous or small-cell lung cancer and various lymphosarcomas.

The instant compounds can be administered orally or parenterally, individually or in combination, preferably parenterally, and usually in the form of a pharmaceutical composition. Parenteral routes of administration include intramuscular, intrathecal, intravenous and intra-arterial. Dosage regimens must be titrated to the particular neoplasm, the condition of the patient, and the response. However, doses generally will be from about 10 to about 100 mg/day for 5-10 days or single daily administration of 250-500 mg., repeated periodically such as every 14 days. Oral dosage forms, including tablets and capsules, contain from 1 to 100 mg. of drug per unit dosage. Isotonic saline solutions containing 1-100 mg/mL can be used for parenteral administration.

Compositions are prepared in a manner well known in the pharmaceutical art and comprise at least one active compound. Accordingly, the present invention also includes pharmaceutical compositions comprising as active ingredient a compound of Formula I, II, III or IV associated with at least one pharmaceutically acceptable carrier, diluent or excipient and the invention further comprises the method of treating susceptible neoplasms using the compositions containing as an active ingredient a compound of Formula I, II, III or IV.

In making the compositions of the present invention, as well as compositions containing other compounds of Formula I, the active ingredients are usually mixed with an excipient, diluted by an excipient or enclosed within such a carrier which can be in the form of a capsule, sachet, paper or other container. When the excipient serves as a diluent, it may be a solid, semi-solid or liquid material which acts as a vehicle, carrier or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum aracia, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form with each dosage normally containing from about 5 mg to about 1 g, more usually about 25 to about 800 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

It will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following examples are provided to further illustrate the invention. It is not intended that the invention be limited in scope by reason of any of the following examples.

In the following examples, the terms melting point, nuclear magnetic resonance spectra, electron impact mass spectra, field desorption mass spectra, fast atom bombardment mass spectra, infrared spectra, ultraviolet spectra, elemental analysis, specific rotation, high performance liquid chromatography and thin layer liquid chromatography are abbreviated m.p., n.m.r., m.s., f.d.m.s., f.a.b.m.s., i.r., u.v., anal., o.r., HPLC, and TLC, respectively. In addition, the adsorption maxima listed for the i.r. spectra are only those of interest and not all of the maxima observed.

The abbreviations THF and DMF stand for tetrahydrofuran and dimethylformamide, respectively.

In conjunction with the n.m.r. spectra, the following abbreviations are used: "s" is singlet, "d" is doublet, "dd" is doublet of doubles, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz. "DMSO-$d_6$" is dimethyl sulfoxide where all protons have been replaced with deuterium.

The n.m.r. spectra were obtained on a Varian Associates EM-390 90 MHz or T-60 60 MHz instrument, on a Jeol Fx-90Q 90 MHz, on a Bruker Corp. 270 MHz instrument or on a General Electric QE-300 300 MHz instrument. The chemical shifts are express in δ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on Cary 118 instrument. Specific rotations were obtained on a Perkin-Elmer Q-41 instrument. Thin layer chromatography was carried out on E. Merck silica gel plates. Melting points are uncorrected.

EXAMPLE 1

A. Preparation of 2-amino-4-chloro-pyrrolo[2,3-d]pyrimidine

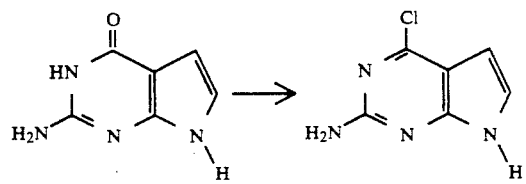

To a 100 ml round bottom flask was charged 2.0 g (13.3 mmol) of 2-amino-7H-pyrrolo[2,3-d]pyrimidin-4-one suspended in 20 ml of phosphorous oxychloride. The reaction was heated to reflux for 2 hr, and after 45 min a yellow solution formed. After cooling to RT, the solvent was removed in vacuo, and the residue was treated with 30 ml of ice water in an ice bath. The insoluble material was filtered away and the filtrate was treated with concentrated NH$_4$OH to adjust the pH to 2. The resulting precipitate was filtered, washed with water and 20 ml of ether, and dried in a vacuum oven to give 1.1 g (49%) of 2-amino-4-Cl-7H-pyrrolo[2,3-d]pyrimidine as a pale yellow solid.

$R_f$=0.15 (5% MeOH/CHCl$_3$)
m.p.=225°-226° C. (dec)
Mass (FD)=169
IR (KBr, cm$^{-1}$)=700, 741, 812, 887, 920, 1203, 1272, 1310, 1385, 1407, 1428, 1485, 1512, 1564, 1616, 1637, 2822, 2927, 2965, 3111, 3190, 3309, 3414, 3450
UV (EtOH) $^l$max=317, 255, 232, 201 (e=6032, 4002, 26867, 11240)
$^1$H NMR (300 MHz, DMSO$_{d6}$) d 622 (d, J=3.3 Hz,1H) 6.46 (s, 2H), 7.06 (d, J=2.7 Hz, 1H), 11.43 (s, 1H)

B. Preparation of 2-pivaloyl-4-chloro-pyrrolo[2,3-d]pyrimidine

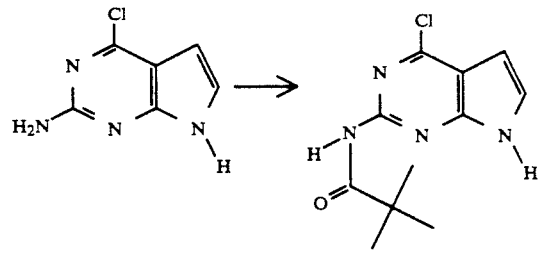

To a 100 ml round bottom flask was charged 4.0 g (23.8 mmol) of 2-amino-4-chloro-7H-pyrrolo[2,3-d]pyrimidine dissolved in 50 ml of anhydrous pyridine. To this solution was added 10.2 ml (83 mmol) of trimethylacetyl chloride, and after several minutes a precipitate began forming. The reaction was stirred at RT under a nitrogen atmosphere for 30 min. The volatiles were removed in vacuo, and the residue was dissolved in 1 L of CHCl$_3$, washed twice with 0.1 N HCl, dried over Na$_2$SO$_4$, and removed in vacuo. The crude residue was flash chromatographed on silica gel eluting with a gradient of 100% CHCl$_3$ to 2% MeOH/CHCl$_3$. After collecting the correct fractions, the solvents were removed in vacuo to give 4.4 g (73%) of 2-pivaloyl-4-chloro-7H-pyrrolo[2,3-d]pyrimidine as an off-white solid.

$R_f$=0.67 (5% MeOH/CHCl$_3$)
m.p.=217°-220°°C. (dec)
Mass (FD)=378
IR (KBr, cm$^{-1}$)=1371, 1390, 1421, 1459, 1493, 510, 1573, 1615, 1694, 2871, 2963, 3127, 3163, 3422

UV (EtOH) $^1$max=278, 241, 201 (e=6553, 24711, 7784)

Anal. Calcd for $C_{11}H_{13}N_4OCl$ : C, 52.28; H, 5.18; N, 2217. Found: C, 52.55; H, 5.18; N, 22.09.

$^1$H NMR (300 MHz, DMSO$_{d6}$) d 1.20 (s, 9H), 6.50 (d, J=3.3 Hz, 1H), 7.51 (d, J=3.2 Hz, 1H), 10.02 (s, 1H), 12.31 (s, 1H)

UV (EtOH) $^1$max=306, 251, 202 (e=4566, 28829, 16387)

$^1$H NMR (300 MHz, DMSO$_{d6}$) d 1.20 (s, 9H), 7.74 (s, 1H), 10.09 (s, 1H), 12.67 (s, 1H)

D. Preparation of diethyl N-[2-pivaloyl-4-chloro-[[pyrrolo[2,3-d]pyrimidin-5-yl]ethynyl]benzoyl]-L-glutamate

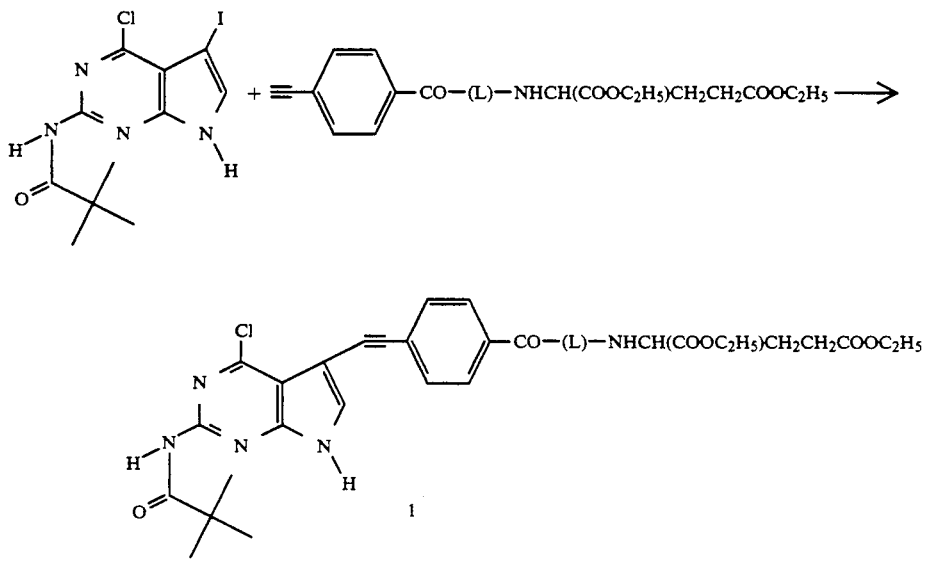

C. Preparation of 2-pivaloyl-4-chloro-5-iodopyrrolo[2,3-d]pyrimidine

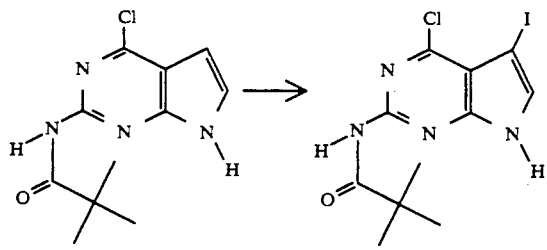

To a 100 ml round bottom flask covered with aluminum foil was charged 1.50 g (5.94 mmol) of 2-pivaloyl-4-chloro-7H-pyrrolo[2,3-d]pyrimidine dissolved in 30 ml of anhydrous THF, followed by the addition of 1.47 g (6.5 mmol) of N-iodosuccinimide. The dark brown solution was stirred at RT under a nitrogen atmosphere for 1 h. The solvent was removed in vacuo, and the residue was dissolved in CHCl$_3$, washed with water, dried over Na$_2$SO$_4$, and removed in vacuo. The crude residue was then flash chromatographed on silica gel eluting with a gradient of 100% CHCl$_3$ to 2% MeOH/CHCl$_3$. After collecting the correct fractions, the solvents were removed in vacuo to give 1.86 g (83%) of 2-pivaloyl-4-chloro-5-iodo-7H-pyrrolo[2,3-d]pyrimidine as a R$_f$=0.47 (5% MeOH/CHCl$_3$)
m.p.=242°-244° C. (dec)
Mass (FD)=378
IR (KBr, cm$^{-1}$)=759, 780, 803, 916, 936, 965, 1021, 1161, 1178, 1227, 1259, 1287, 1315, 1368, 1414, 1453, 1500, 1565, 1603, 1708, 2871, 2967, 3213, 3425

To a 100 ml round bottom flask covered with aluminum foil were charged 1.5 g (3.96 mmol) of 2-pivaloyl-4-chloro-5-iodo-7H-pyrrolo[2,3-d]pyrimidine, 1.38 g (4.16 mmol) of diethyl p-ethynyl-N-benzoyl-L-glutamate, 0.16 g (0.83 mmol) of copper (I) iodide, and 0.48 g (0.42 mmol) of tetrakis(triphenylphoshine)palladium(0) dissolved in 30 ml of anhydrous DMF, followed by the addition of 1.16 ml (8.3 mmol) of triethylamine. The dark brown solution was stirred at RT under a nitrogen atmosphere for 4 h. The volatiles were removed in vacuo and the crude residue was flash chromatographed on silica gel eluting with a gradient of 100% CHCl$_3$ to 1% MeOH/CHCl$_3$. After collecting the correct fractions, the solvents were removed in vacuo, and the solid was triturated in 40 ml of a 2:1 mixture of hexanes/ether to give 1.35 g (58%) of 1 as a tan solid.

R$_f$=0.22 (5% MeOH/CHCl$_3$)
m.p.=212°-214° C. (dec)
Mass (FD)=582
IR (KBr, cm$^{-1}$)=785, 851, 926, 1020, 1099, 1162, 1300, 1426, 1497, 1568, 1612, 1639, 1737, 2219, 2978, 3214
UV (EtOH) $^1$max=315, 257, 203 (e=19105, 20190, 24301)
Anal. Calcd for $C_{29}H_{32}N_5O_6Cl$ : C, 59.84; H, 5.54; N, 12.03. Found : C, 59.54; H, 5.52; N, 11.83.
$^1$H NMR (300 MHz, DMSO$_{d6}$) d 1.00-1.19 (m, 6H), 1.21 (s, 9H(, 197-213 (m, 2H), 2.40-2.47 (m, 2H), 4.43 (m, 1H), 7.60 (d, J=8.2 Hz, 2H), 7.90 (d, J=8.2 Hz, 2H), 8.80 (d, 7.3 Hz, 1H), 10.14 (s, 1H), 12.80 (s, 1H)

E. Preparation of diethyl N-[2-pivaloyl-4-chloro-[[pyrrolo[2,3-d]pyrimidin-5-yl]ethyl]benzoyl]-L-glutamate

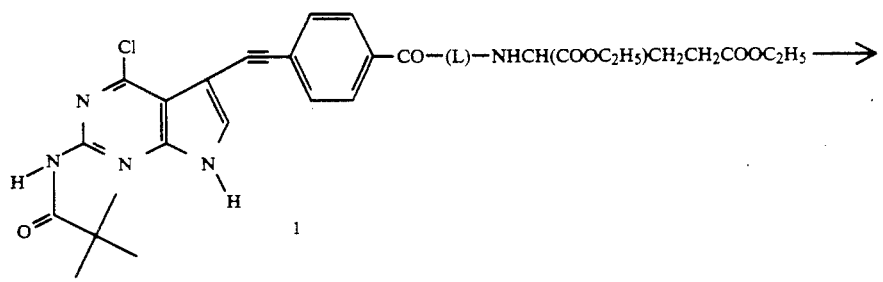

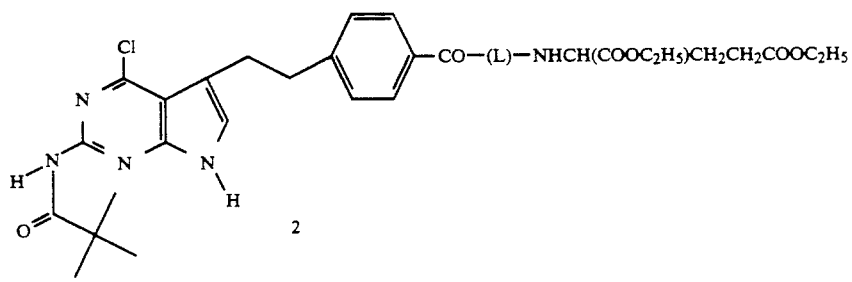

To a 50 ml round bottom flask was charged 0.050 g ( 0.086 mmol) of 1 dissolved in 1 ml of absolute ethanol and 1 ml of dichloromethane, followed by the addition of 0.04 g of 10% Pd/C catalyst. The reaction mixture was then stirred under a balloon containing hydrogen for 4 h. The catalyst was filtered, washed thoroughly, and the filtrate was removed in vacuo. The crude residue was then flash chromatographed on silica gel eluting with 2% MeOH/CHCl$_3$. After collecting the correct fractions, the solvents were removed in vacuo to give 0.45 g (95%) of 2 as a yellow solid.

$R_f$=0.47 (5% MeOH/CHCl$_3$)
m.p=86°-88° C.
Mass (FAB)=586
IR (KBr, cm$^{-1}$)=759, 922, 1020, 1098, 1165, 1374, 1427, 1469, 1502, 1540, 1569, 1613, 1648, 1737, 2977, 3244
UV (EtOH) $^1$max=248, 203 (e=40126, 36298)
$^1$H NMR (300 MHz, DMSO$_{d6}$) d 1.11–1.19 (m, 6H), 1.20 (s, 9H), 1.95–2.09 (m, 2H), 2.41 (t, J=7.4 Hz, 2H), 2.97–3.15 (m, 4H), 3.98–4.11 (m, 4H), 4.38 (m, 1H), 7.23 (s, 1H), 7.32 (d, J=8.1 Hz, 2H), 7.78 (d, J=8.0 Hz, 2H), 8.63 (d, J=8.0 Hz, 1H), 9.98 (s, 1H), 12.02 (s, 1H)

F. Preparation of N-[1-amino-4-chloro-[[pyrrolo[2,3-d]pyrimidin-5-yl]ethyl]benzoyl]-L-glutamic acid

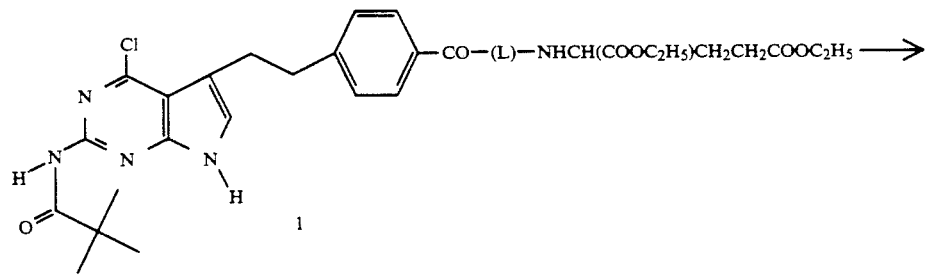

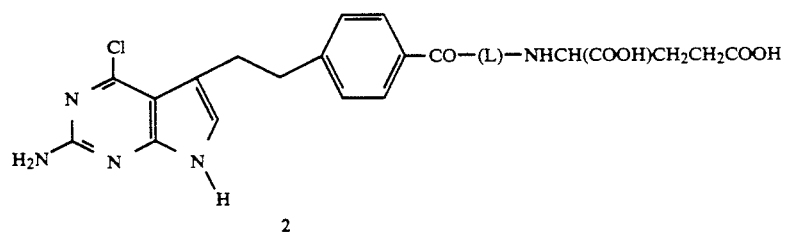

To a 15 ml round bottom flask was charged 0.015 g (0.026 mmol) of 1 suspended in 1 ml of 2 N NaOH. The mixture was stirred at RT for 7 days, and then at 50° C. for 4 h. The pale yellow solution was acidified with 5 N HCl, and the white prepitate was cooled in an ice bath, filtered, washed with 15 ml of water, and dried in a vacuum oven at 70° C. to give 0.0056 g (49%) of 2 as a tan solid.

$R_f$=0.05 (50% MeOH/CHCL$_3$)
m.p.=>300° C. (dec)
Mass (FAB)=446
IR (KBr, cm$^{-1}$)=599, 928, 1020, 1225, 1435, 1501, 1555, 1617, 1714, 3337
UV (EtOH) $^1$max =322, 239, 202 (e=4085, 38829, ¹H NMR (300 MHz, DMSO$_{d6}$) d 1.87-2.09 (m, 2H), 2.32 (t, J=7.3 Hz, 2H), 2.95 (s, 4H), 4.36 (m, 1H), 6.42 (s, 2H), 6.78 (s, 1H), 7.30 (d, J=7.7 Hz, 2H), 7.81 (d, J=7.6 Hz, 2H), 8.49 (d, J=7.2 Hz, 1H), 11.13 (s, 1H), 12.40 (br s, 2H

EXAMPLE 2

A. Preparation of diethyl N-[2-pivaloyl-4-mercapto[[-pyrrolo[2,3-d]pyrimidin-5-yl]ethyl]benzoyl]-L-glutamate fractions, the solvents were removed in vacuo to give 0.11 g (50%) of 2 as a yellow solid.

R$_f$=0.39 (5% MeOH/CHCL$_3$)
m.p.=185-187° C. (dec)
Mass (FD)=583
IR (KBr, cm$^{-1}$)=766, 842, 935, 1023, 1163, 1360, 1439, 1564, 1640, 1735, 2975, 3195
UV (EtOH) $\lambda$max =339, 279, 238, 202 (e=16995, 10601, 34456, 43227)
Anal. Calcd for C$_{20}$H$_{37}$N$_5$O$_6$S : C, 59.67; H, 6.39; N, 12.00. Found: C, 59.44; H, 6.33; N, 11.91.

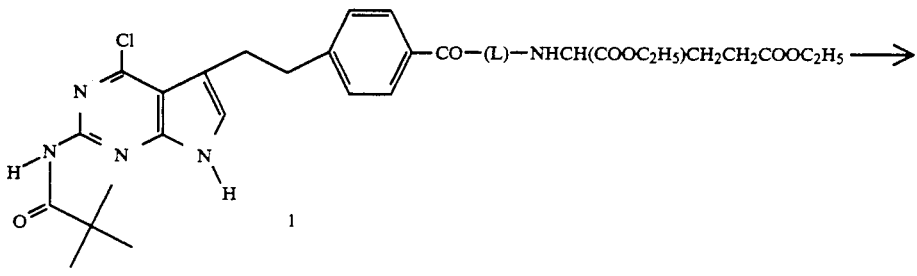

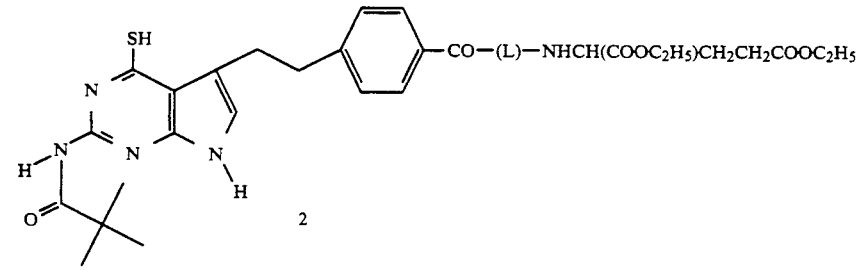

To a 15 ml round bottom flask was charged 0.22 g (0.37 mmol) of 1 dissolved in 4 ml of anhydrous 2-methoxyethanol, followed by the addition of 0.20 g (2.6 mmol) of thiourea. The reaction mixture was heated to 100° C. under a nitrogen atmosphere for 20 min. After cooling to RT, the solvent was removed in vacuo. The residue was then dissolved in 100 ml CHCL$_3$, washed with water, and the organic layer was separated away, dried over Na$_2$SO$_4$, and removed in vacuo. This residue was then flash chromatographed on silica gel eluting with 2% MeOH/CHCL$_3$. After collecting the correct ¹H NMR (300 MHz, DMSO$_{d6}$) d 1.11-1.24 (m, 15H), 1.90-2.10 (m, 2H), 2.41 (t, J=7.4 Hz, 2H), 2.98-3.03 (m, 2H), 3.14-3 22 (m, 2H), 3.99-4.11 (m, 4H), 4.38-4.40 (m, 1H), 6.88 (s, 1H), 7.33 (d, J=8.1 Hz, 2H), 7.77 (d, J=8.1 Hz, H), 8.62, (d, J=7.4 Hz, 1H), 11.05 (s, 1H), 11.62 (s, 1H), 13.14 (s, 1H)

B. Preparation of N-[2-amino-4-mercapto-[pyrrolo[2,3-d]pyrimidin-5-yl]ethyl]benzoyl]-L-glutamic acid

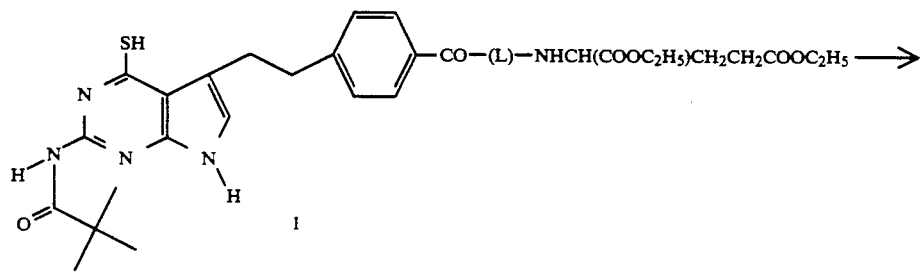

-continued

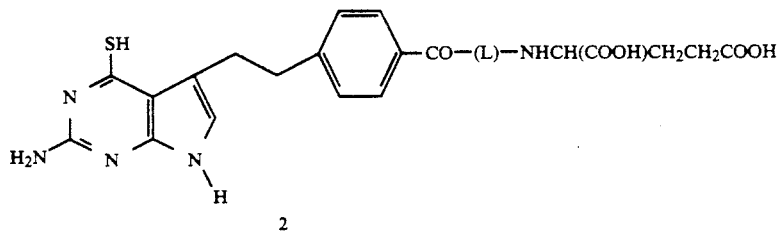

To a 15 ml round bottom flask was charged 0.083 g (0.14 mmol) of 1 dissolved in 6 ml of 0.5 N NaOH. The reaction was covered with aluminum foil and stirred at RT for 5.5 days. The orange solution was then acidified with 1 N HCl, and the precipitate was cooled down in an ice bath, filtered, washed with water, and dried in a vacuum oven at 60° C. to give 0.037 g (59%) of 2 as a tan solid.

$R_f$=0.04 (50% MeOH/CHCL$_3$)
m.p.=240°-242° C. (dec)
Mass (FAB)=444
IR (KBr, cm$^{-1}$)=767, 817, 968, 1020, 1098, 1191, 1343, 1402, 1446, 1502, 1568, 1637, 1710, 2929, 3333
UV (EtOH) $^1$max=347, 238, 203 (e=9999, 30880, 40868)
Anal. Calcd for $C_{20}H_{21}N_5O_5S$ : C, 54.17; H, 4.77; N, 15.79. Found: C, 53.90; H, 4.73; N, 15.52.
$^1$H NMR (300 MHz, DMSO$_{d6}$) d 2.22-2.35 (m, 4H), 2.94-3.20 (m, 4H), 4.29-4.31 (m, 1H), 6.39 (s, 2H), 6.52 (s, 1H), 7.30 (d, J=7.9 Hz, 2H), 7.73 (d, J=7.9 Hz, 2H), 8.48 (d, J=7.5 Hz, 1H), 10.95 (s, 1H)

EXAMPLE 3

A. Preparation of diethyl N-[2-pivaloyl-[[pyrrolo[2,3-d]pyrimidin-5-yl]ethyl]benzoyl]-L-glutamate and 2 ml of dichloromethane, followed by the addition of 0.05 ml (1.3 mmol) of concentrated ammonium hydroxide. To this solution was added 0.20 g of 10% Pd/C catalyst, and the mixture was hydrogenated at 50 psi for 20 h. The catalyst was filtered and washed thoroughly, and the filtrate was removed in vacuo. The residue was then flash chromatographed on silica gel eluting with a gradient of 100% CHCL$_3$ to 2% MeOH/CHCL$_3$. After collecting the correct fractions, the solvents were removed in vacuo to give 0.055 g (59%) of 2 as a pale yellow solid.

$R_f$=0.33 (5% MeOH/CHCL$_3$)
m.p.=148°-149° C.
Mass (FD)=551
IR (KBr, cm$^{-1}$)=766, 850, 923, 1021, 1097, 1165, 433, 1477, 1500, 1545, 1582, 1613, 1636, 1701, 1742, 2978, 3225, 3363, 3441
UV (EtOH) $^1$max =246, 203 (e=38574, 36571)
Anal. Calcd for $C_{20}H_{37}N_5O_6$ : C, 63.14; H, 6.76; N, 12.69. Found: C, 63.02; H, 6.75; N, 12.39.
$^1$H NMR (300 MHz, DMSO$_{d6}$) d 1.11-1.20 (m, 15H), 1.90-2.10 (m, 2H), 2.41 (t, J=7.4 Hz, 2H), 3.01 (s, 4H), 3.99-4.12 (m, 4H), 4.38-4.41 (m, 1H), 7.14 (s, 1H), 7.32 (d, J=8.0 Hz, 2H), 7.76 (d, J=7.9 Hz, 2H), 8.60 (d, J=7.3 Hz, 1H), 9.69 (s, 1H), 11.57 (s, 1H)

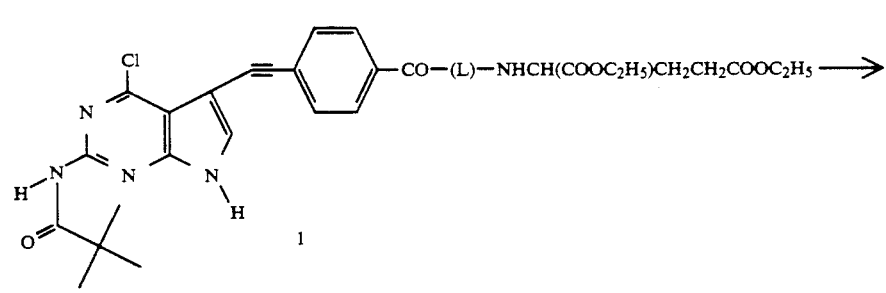

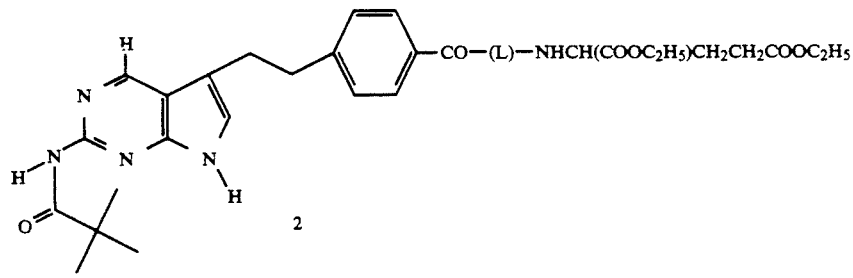

To a Parr hydrogenation bottle was charged 0.10 g (0.17 mmol) of 1 dissolved in 8 ml of absolute ethanol B. Preparation of N-[2-amino-[[pyrrolo[2,3-d]pyrimidin-5-yl]ethyl]benzoyl]-L-glutamic acid

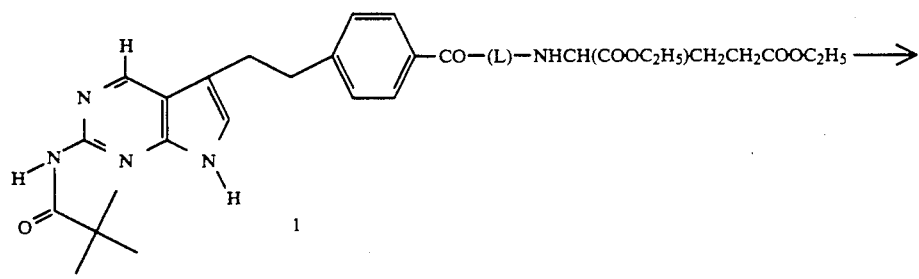

To a 15 ml round bottom flask was charged 0.045 g (0.082 mmol) of 1 suspended in 2 ml of 1 N NaOH. The reaction was stirred at RT for 7 days. The yellow solution was acidified with 1 N HCl, and the precipitate was cooled down in an ice bath, filtered, washed with water, and dried in a vacuum oven at 70° C. to give 0.019 g (57%) of 2 as a pale yellow solid.

$R_f$=0.05 (50% MeOH/CHCL$_3$)
m.p.=260°-264° C. (dec)
Mass (FAB)=412
IR (KBr, cm$^{-1}$)=845, 963, 1020, 1093, 1209, 1291, 1333, 1404, 1451, 1500, 1538, 1558, 1614, 1655, 2813, 2857, 2947, 3138, 3353
UV (EtOH) $\lambda$max =318, 237, 203 (e=2239, 24103, 25087)
$^1$H NMR (300 MHz, DMSO$_{d6}$) d 1.87-2.09 (m, 2H), 2.30-2.34 (m, 2H), 2.90-3.01 (m, 4H), 4.32-4.39 (m, 1H), 6.01 (s, 2H), 6.70 (s, 1H), 7.30 (d, J=8.1 Hz, 2H), 7.76 (d, J=8.1 Hz, 2H), 8.41 (s, 1H), 8.50 (d, J=7.6 Hz, 1H), 10.76 (s, 1H), 12.40 (br s, 1H)

EXAMPLE 4

A. Preparation of diethyl N-[2-pivaloyl-[[dihydropyrrolo[2,3-d]pyrimidin-5-yl]ethyl]benzoyl]-L-glutamate

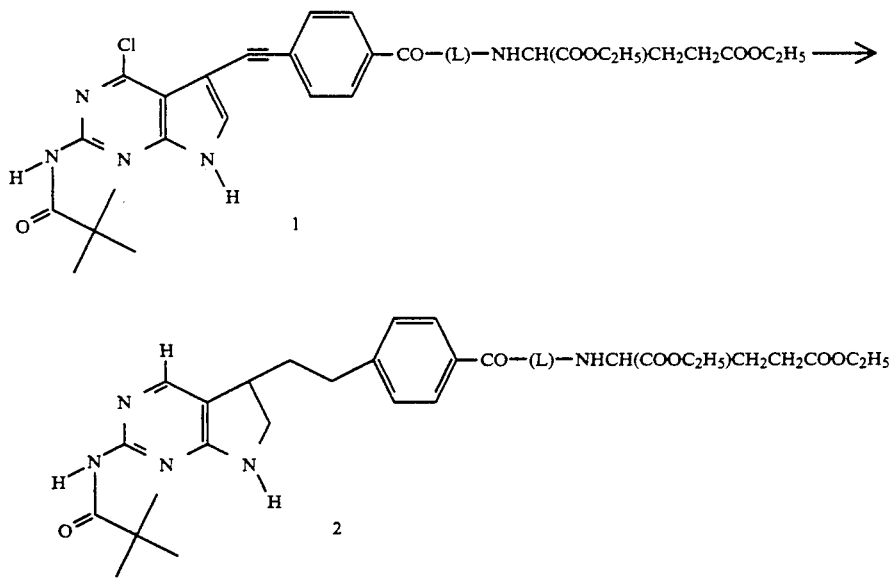

To a Parr hydrogenation bottle was charged 0.068 g (0.17 mmol) of 1 dissolved in 6 ml of absolute ethanol and 1 ml of dichloromethane, followed by the addition of 0.2 g of 10% Pd/C catalyst. This mixture was then hydrogenated at 50 psi for 18 h. After filtering and washing the catalyst thoroughly, the filtrate was removed in vacuo. The crude residue was then flash chromatographed on silica gel eluting with 2% MeOH/CHCL$_3$. After collecting the correct fractions, the solvents were removed in vacuo to give 0.022 g (34%) of 2 as a white solid.

$R_f$=0.23 (5% MeOH/CHCL$_3$)
m.p.=90°-92° C.
Mass (FD)=554

IR (KBr, cm$^{-1}$)=853, 925, 1022, 1181, 1398, 1504, 1591, 1623, 1735, 2978, 3308

UV (EtOH) $\lambda$max =296, 222, 203 ($\epsilon$=7464, 31504, 35543)

Anal. Calcd for $C_{29}H_{39}N_5O_6$: C, 62.91; H, 7.10; N, 12.65. Found: C, 62.61; H, 7.40; N, 12.53.

$^1$H NMR (300 MHz, DMSO$_{d6}$) d 1.04–1.20 (m, 15H), 1.75–1.85 (m, 1H), 1.93–2.09 (m, 4H), 2.41 (t, J=7.4 Hz, 2H), 2.69 (t, J=7.6 Hz, 3H), 3.65–3.69 (m, 1H), 4.00–4.11 (m, 4H), 4.39–4.42 (m, 1H), 7.34 (d, J=8.0 Hz, 2H), 7.40 (s, 1H), 7.78 (d, J=8.4 Hz, 2H), 7.81 (s, 1H), 8.62 (d, J=7.4 Hz, 1H), 9.29 (br s, 1H)

B. Preparation of N-[2-amino-[[dihydropyrrolo[2,3-d]pyrimidin-5-yl]ethyl]benzoyl]-L-glutamic acid

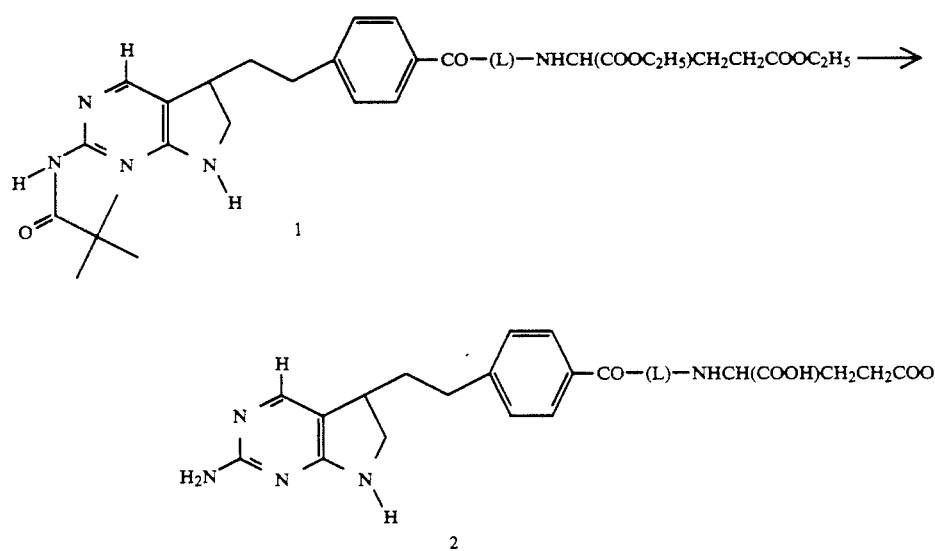

To a 15 ml round bottom flask was charged 0.075 g (0.13 mmol) of 1 suspended in 3 ml of 1 N NaOH. The reaction was covered with aluminum foil and stirred at RT for 7.5 days. The yellow solution was acidified with 5 N HCl, and the yellow precipitate was cooled down in an ice bath, filtered, washed with water and dried in a vacuum oven at 70° C. The filtrate was removed in vacuo, and the the residue was purified by C-18 reverse phase chromatography eluting with 10% MeCN/89.5% H$_2$O/0.5% AcOH. The correct fractions were combined, and the solvents were concentrated in vacuo to near dryness and then lyophilized. The precipitated solid and the lyophilized solid were combined to give 0.027 g (48%) of 2 as a pale yellow solid.

R$_f$=0.07 (50% MeOH/CHCL$_3$)
m.p.=>300° C. (dec)
Mass (FAB)=414
IR (KBr, cm$^{-1}$)=660, 1180, 1295, 1380, 1500, 1608, 1630, 1640, 2920, 3340

UV (EtOH) $\lambda$max =238, 203 ($\epsilon$=8086, 15837)

$^1$H NMR (300 MHz, DMSO$_{d6}$) d 1.89–1.99 (m, 1H), 2.10–2.20 (m, 4H), 2.26 (t, J=6.8 Hz, 3H), 2.61–2.66 (m, 2H), 4.30–4.40 (m, 1H), 5.76 (br s, 2H), 6.77 (s, 1H), 7.29 (d, J=7.9 Hz, 2H), 7.51 (br s, 1H), 7.72 (d, J=7.7 Hz, 2H), 8.10 (br s, 1H)

EXAMPLE 5

A. Preparation of 2-amino-4-methoxy-pyrrolo[2,3-d]pyrimidine

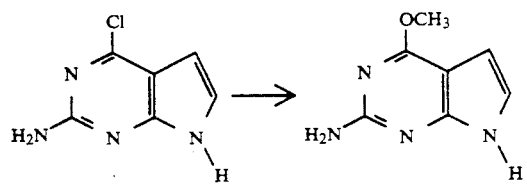

To a 250 ml round bottom flask under a nitrogen atmosphere was charged 2.0 g (11.9 mmol) of 2-amino-4-Cl-7H-pyrrolo[2,3-d]pyrimidine to a stirring solution of 0.92 g (40 mmol) of sodium metal dissolved in 80 ml anhydrous methanol. The yellow solution was heated to reflux for 24 h. After cooling to RT, the reaction was neutralized with glacial acetic acid to a pH of 6.0, and the volatiles were removed in vacuo. The residue was treated with 50 ml of water, and a small amount of an insoluble solid was filtered away. The filtrate was extracted three times with 100 ml CHCL$_3$, and the organic washes were combined, dried over Na$_2$SO$_4$, and removed in vacuo. The crude solid was flash chromatographed on silica gel eluting with 5% MeOH/CHCL$_3$. After collecting the the correct fractions, the solvents were removed in vacuo to give 1.36 g (70%) of 2-amino-4-methoxy-7H-pyrrolo[2,3-d]pyrimidine as an off-white solid.

R$_f$=0.17 (5% MeOH/CHCL$_3$)
m.p=202°–204° C. (dec)
Mass (FD)=164
IR (KBr, cm$^{-1}$)=711, 740, 793, 823, 902, 1056, 1093, 1165, 1194, 1228, 1321, 1334, 1390, 1406, 1440, 1473, 1490, 1579, 1610, 1632, 2828, 3110, 3370, 3484

UV (EtOH) $\lambda$max=287, 257, 223 ($\epsilon$=7287, 7375, 24330)

Anal. Calcd for C$_7$H$_8$N$_4$O: C, 51.22; H, 4.91; N, 34.13. Found: C, 51.02; H, 4.95; N, 34.23.

$^1$H NMR (300 MHz, DMSO$_{d6}$) $\delta$ 3.88 (s, 3H), 5.96 (s, 2H), 6.15 (d, J=2.3 Hz, 1H), 6.78 (d, J=2.9 Hz, 1H), 10.99 (s, 1H)

B. Preparation of 2-pivaloyl-4-methoxy-pyrrolo[2,3-d]pyrimidine

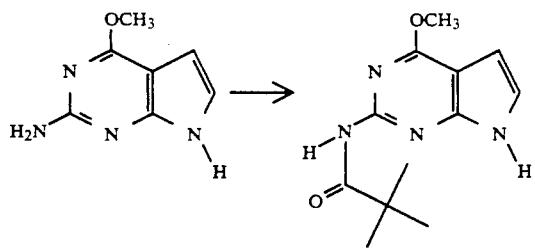

To a 50 ml round bottom flask was charged 0.90 g (5.48 mmol) of 2-amino-4-methoxy-7H-pyrrolo[2,3-pyrimidine dissolved in 12 ml of anhydrous pyridine. To this solution was added 2.4 ml (19.2 mmol) of trimethylacetyl chloride. The reaction was heated to reflux for 1.5 h under a nitrogen atmosphere. The volatiles were removed in vacuo, and the residue was dissolved in 9 ml of methanol and cooled down in an ice bath. To this stirring solution was added 9 ml of 10% ammonium hydroxide and the resulting precipitate formed was filtered, washed with water and 10% ammonium hydroxide, and dried to give 1.09 g (80%) of 2- pivaloyl-4-methoxy-7H-pyrrolo[2,3-d]pyrimidine as a white solid.

$R_f$=0.26 (5% MeOH/CHCL$_3$)

m.p.=235°–236° C.

Mass (FD)=248

IR (KBr, cm$^{-1}$)=709, 720, 738, 789, 844, 881, 901, 934, 969, 1017, 1049, 1058, 1100, 1167, 1209, 1309, 1358, 1395, 1460, 1516, 1588, 1618, 1693, 2958, 3130, 3185, 3430

UV (EtOH) $^1$max =278, 231, 202 (e=12328, 19978, 18292)

Anal. Calcd for C11H13N4OCl : C, 58.05; H, 6.50; N, 22.57. Found : C, 57.75; H, 6.48; N, 22.62.

$^1$H NMR (300 MHz, DMSO$_{d6}$) d 1.20 (s, 9H), 6.38 (d, J=3.2 Hz, 1H), 7.20 (d, J=3.1 Hz, 1H), 9.49 (s, 1H), 11.77 (s 1H)

C. Preparation of 2-pivaloyl-4-methoxy-5-iodopyrrolo[2,3-d]pyrimidine

To a 15 ml round bottom flask covered with aluminum foil was charged 0.266 g (1.07 mmol) of 2-pivaloyl-4-methoxy-7H-pyrrolo[2,3-d]pyrimidine dissolved in 6 ml of anhydrous THF. The reaction was stirred under a nitrogen atmosphere for 1.5 h. The solvent was removed in vacuo, and the residue was dissolved in 100 ml of CHCL$_3$, washed with water, and the organic layer was separated away, dried over Na$_2$SO$_4$, and removed in vacuo. The crude residue was then flash chromatographed on silica gel eluting with a gradient of 100% CHCL$_3$ to 1% MeOH/CHCL$_3$. After collecting the correct fractions, the solvents were removed in vacuo to give 0.33 g (82%) of 2-pivaloyl-4-methoxy-5-iodo-7H-pyrrolo[2,3-d]pyrimidine as an off-white solid.

$R_f$=0.50 (5% MeOH/CHCL$_3$)

m.p.=243°–244° C. (dec)

Mass (FD)=374

IR (KBr, cm$^{-1}$)=652, 723, 785, 806, 843, 965, 1010, 1096, 1175, 1212, 1253, 1279, 1328, 1390, 1426, 1461, 1532, 1579, 1620, 1705, 2955, 3200, 3435

UV (EtOH) $^1$max =283, 242, 202 (e=10018, 30658, 19457)

$^1$H NMR (300, DMSO$_{d6}$) d 1.20 (s, 9H), 4.01 (s, 3H), 7.40 (d, J=2.0 Hz, $^1$H), 9.55 (s, 1H), 12.11 (s, 1H)

D. Preparation of diethyl N-[2-pivaloyl-4-methoxy-[[pyrrolo[2,3-d]pyrimidin-5-yl]ethynyl]benzoyl]glutamate

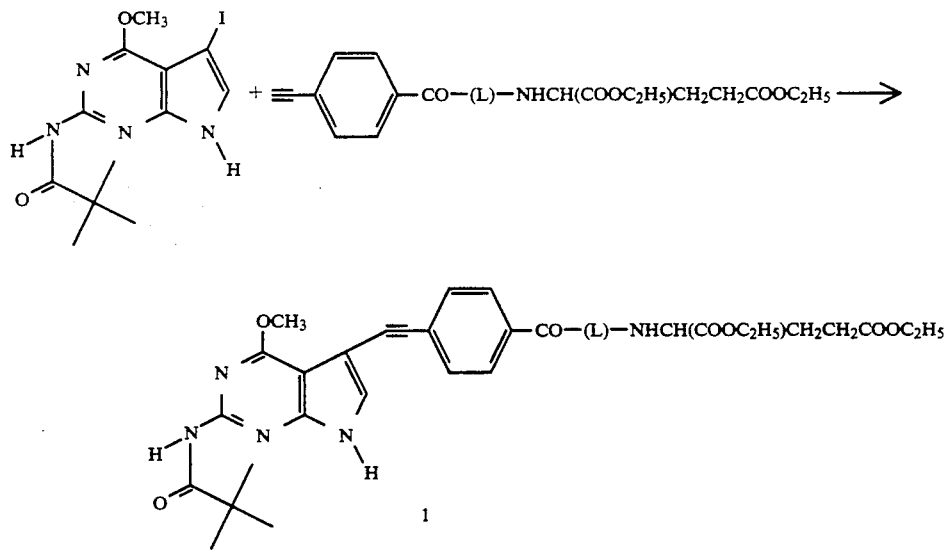

To a 25 ml round bottom flask covered with aluminum foil were charged 0.20 g (0.53 mmol) of 2-pivaloyl-4-methoxy-5-iodo-7H-pyrrolo[2,3-d]pyrimidine, 0.19 g (0.58 mmol) of diethyl p-ethynyl-N-benzoyl-L-glutamate, 0.024 g (0.13 mmol) of copper (I) iodide, and 0.074 g (0.06 mmol) of tetrakis(triphenylphosphine)palladium(0) suspended in 5 ml of anhydrous DMF, followed by the addition of 0.18 ml (1.28 mmol) of triethylamine. The dark brown mixture was stirred and heated under a nitrogen atmosphere at 50° C. for 0.5 h. The volatiles were removed in vacuo, and the crude residue was flash chromatographed on silica gel eluting with a gradient of 100% $CHCL_3$ to 1% $MeOH/CHCL_3$. After collecting the correct fractions, the solvents were removed in vacuo to give 0.085 g (28%) of 1 as a tan solid.

$R_f$=0.48 (2% $MeOH/CHCL_3$)
m.p.=215°-216° C. (dec)
Mass (FD)=577
IR (KBr, $cm^{-1}$)=792, 852, 1097, 1165, 1346, 1430, 1527, 1607, 1737, 2216, 2978, 3210
UV (EtOH) $\lambda max$ =321, 263, 254, 201 (e=22757, 22713, 23239, 39466)
$^1$H NMR (300 MHz, $DMSO_{d6}$) d 1.06–1.21 (m, 15H), 1.97–2.11 (m, 2H), 2.41–2.51 (m, 2H), 3.99–4.13 (m, 7H), 4.38–4.45 (m, 1H), 7.56 (d, J=8.2 Hz, 2H), 7.61 (s, 1H), 7.90 (d, J=8.1 Hz, 2H), 8.79 (d, J=7.3 Hz, 1H), 9.61 (s, 1H), 12.28 (s, 1H)

E. Preparation of diethyl N-[2-pivaloyl-4-methoxy-[[pyrrolo[2,3-d]pyrimidin-5-yl]ethyl]benzoyl]glutamate To a 50 ml round bottom flask was charged 0.075 g (0.13 mmol) of 1 dissolved in 8 ml of absolute ethanol and 2 ml of dichloromethane, followed by the addition of 0.05 g of 10% Pd/C catalyst. The reaction mixture was then stirred under a balloon containing hydrogen for 6 h. The catalyst was filtered, washed thoroughly, and the filtrate was removed in vacuo. The crude residue was then flash chromatographed on silica gel eluting with 3% $MeOH/CHCL_3$. After collecting the correct fractions, the solvents were removed in vacuo to give 0.062 g (82%) of 2 as a yellow solid.

$R_f$0.35 (5% $MeOH/CHCL_3$)
m.p.=71°-74° C. (dec)
Mass (FAB)=582
IR (KBr, $cm^{-1}$)=793, 844, 970, 1020, 1095, 1168, 1338, 1587, 1615, 1648, 1737, 2979, 3259
UV (EtOH) $\lambda max$ =277, 238, 202(e=13505, 35834, 45830)
$^1$H NMR (300 MHz, $DMSO_{d6}$) d 1.06–1.20 (m, 15H), 1.95–2.09 (m, 2H), 2.41–2.51 (m, 4H), 2.95 (s, 2H), 3.98–4.11 (m, 7H), 4.36–4.40 (m,1H), 6.89 (s, 1H), 7.28 (d, J=8.1 Hz, 2H), 7.76 (d, J=8.0 Hz, 2H), 8.62 (d, J=7.4 Hz, 1H), 9.47 (s, 1H), 11.43 (s, 1H)

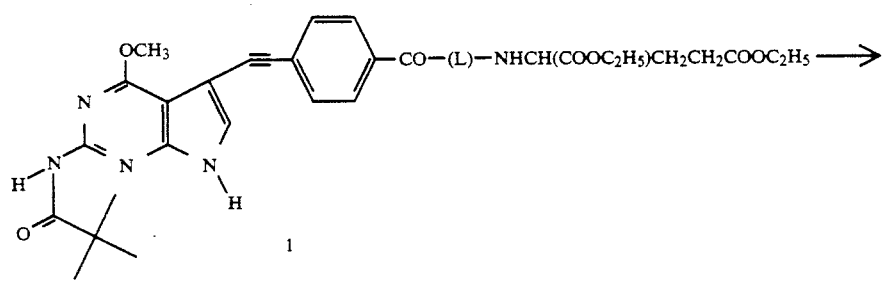

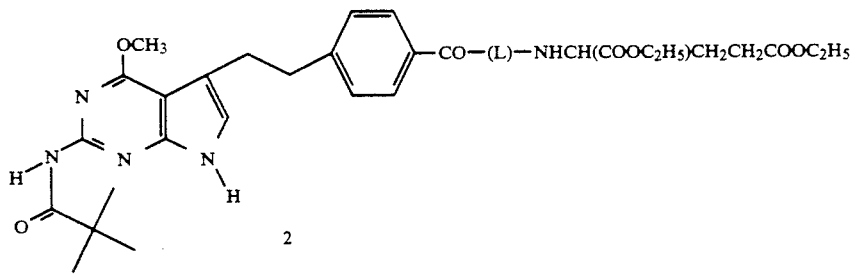

F. Preparation of N-[2-amino-4-methoxy-[[pyrrolo[2,3-d]pyrimidin-5-yl]ethyl]benzoyl]glutamic acid

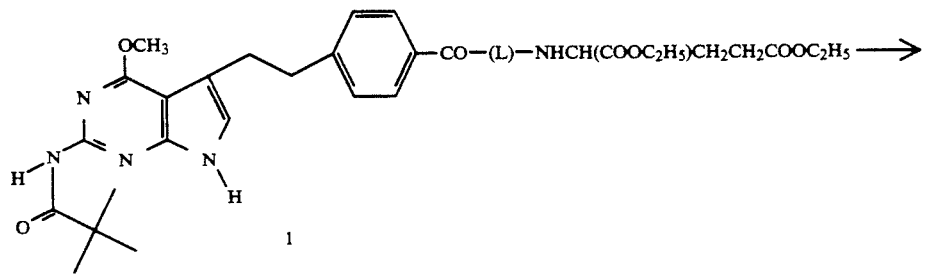

-continued

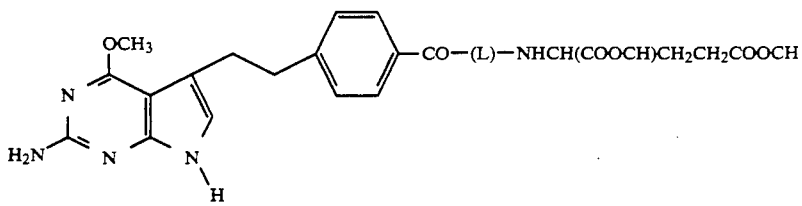

2

To a 15 ml round bottom flask was charged 0.07 g (0.12 mmol) of 1 suspended in 4 ml of 0.5 N NaOH. The mixture was stirred at RT for 7 days. The pale yellow solution was then acidified with 1 N HCl, and the tan precipitate was cooled in an ice bath, filtered, washed with water, and dried in a vacuum oven at 70° C. to give 0.044 g (83%) of 2 as a tan solid.

R$_f$=0.08 (50% MeOH/CHCL$_3$)
m.p.=230° C. (dec)
Mass (FAB)=442
IR (KBr, cm$^{-1}$)=777, 958, 1020, 1090, 1153, 1197, 1250, 1394, 1441, 1483, 1538, 1614, 1660, 2941, 3336
UV (EtOH) $^1$max =230, 203 (e=35345, 34328)
$^1$H NMR (300 MHz, DMSO$_{d6}$) d 1.90–2.07 (m, 2H), 2.32 (t, J=7.3 Hz, 2H), 2.84–2.95 (m, 4H), 3.96 (s, 3H), 4.33–4.40 (m, 1H), 6.56 (s, 1H), 7.26 (d, J=8.0 Hz, 2H), 7.78 (d, J=8.1 Hz, 2H), 8.50 (d, J=7.6 Hz, 1H), 11.04 (s, 1H), 12.40 (br s, 2H)

EXAMPLE 6

A. Preparation of 2-pivaloyl-4-chloro-5-(trimethylsilyl)acetylene-pyrrolo[2,3-d]pyrimidine

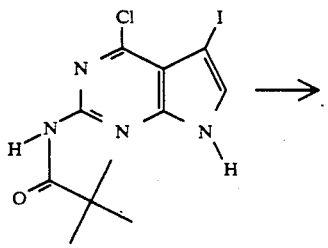

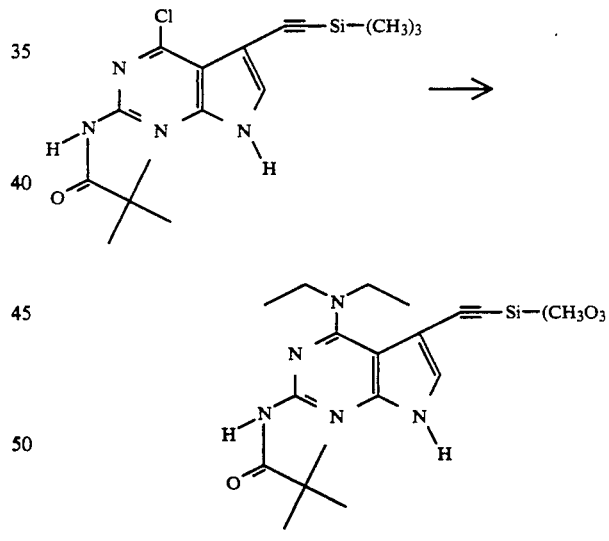

To a 100 ml round bottom flask covered with aluminum foil were charged 1.0 g (2.6 mmol) of 2-pivaloyl-4-chloro-5-iodo-7H-pyrrolo[2,3-d]pyrimidine, 0.2 g (1.04 mmol) of copper (I) iodide, 1.8 ml (13 mmol) of (trimethylsilyl)acetylene, and 0.30 g (0.26 mmol) of tetrakis(-triphenylphosphine)palladium(0) dissolved in 15 ml of anhydrous DMF, followed by the addition of 0.72 ml (5.1 mmol) of triethylamine. The dark brown solution was stirred at RT under a nitrogen atmosphere for 18 h. The volatiles were removed in vacuo, and the residue was dissolved in 1 L of CHCL$_3$, washed with water, and the organic layer was separated away, dried over Na$_2$SO$_4$, and removed in vacuo. The crude was then flash chromatographed on silica gel eluting with a gradient of 100% CHCL$_3$ to 1% MeOH/CHCL$_3$. After collecting the correct fractions, the solvents were removed in vacuo to give 0.49 g (54%) of 2-pivaloyl-4-chloro-5-(trimethylsilyl)acetylene-7H-pyrrolo[2,3-d]pyrimidine as a tan solid.

R$_f$=0.45 (5% MeOH/CHCL$_3$)
m.p.=>300° C.
Mass (FD)=348
IR (KBr, cm$^{-1}$)=626, 758, 785, 860, 926, 1021, 1166, 232, 1260, 1291, 1432, 1456, 1498, 1568, 1610, 1698, 2161, 961, 3154, 3424
UV (EtOH) $^1$max =261, 256, 201 (e=29006, 29104, 0753)
$^1$H NMR (300 MHz, DMSO$_{d6}$) d 0.21 (s, 9H), 1.20 (s, 9H), 7.89 (s, 1H), 10.12 (s, 1H), 12.67 (s, 1H)

B. Preparation of 2-pivaloyl-4-diethylamino-5-(trimethylsilyl)acetylene-pyrrolo[2,3-d]pyrimidine To a 100 ml round bottom flask under a nitrogen o atmosphere was charged 0.49 g (1.4 mmol) of 2-pivaloyl-4-chloro-5-(trimethylsilyl)acetylene-7H-pyrrolo[2,3-d]pyrimidine suspended in 15 ml of anhydrous 2-methoxyethanol, followed by the addition of 0.87 ml (8.4 mmol) of diethylamine. The mixture was heated to 100° C. for 1 h. The volatiles were removed in vacuo, and the residue was flash chromatographed eluting with 3% MeOH/CHCL$_3$. After collecting the correct fractions, the solvents were removed in vacuo to give 0.43 g (80%) of 2-pivaloyl-4-diethylamino-5-(trimethylsily-)acetylene-7H-pyrrolo[2,3-d]pyrimidine as a tan solid.

R$_f$=0.43 (5% MeOH/CHCl$_3$)
m.p.=191°–194° C. (dec)

Mass (FD)=385

IR (KBr, cm$^{-1}$)=6,95, 711, 759, 838, 862, 1040, 1064, 1095, 1176, 1209, 1250, 1304, 1357, 1427, 1532, 1573, 1690, 2144, 2962, 3108, 3428

UV (EtOH) $^1$max=367, 296, 237, 207, 203 (e=966, 18048, 28781, 22099, 21727)

$^1$H NMR (300, DMSO$_{d6}$) d 0.19 (s, 9H), 1.13–1.18 (m, 15H), 3.86 (q, J=6.8 Hz, 4H), 7.62 (s, 1H), 9.08 (s, 1H), 11.88 (s, 1H)

C. Preparation of 2-pivaloyl-4-diethylamino-5-acetylene-pyrrolo[2,3-d]pyrimidine

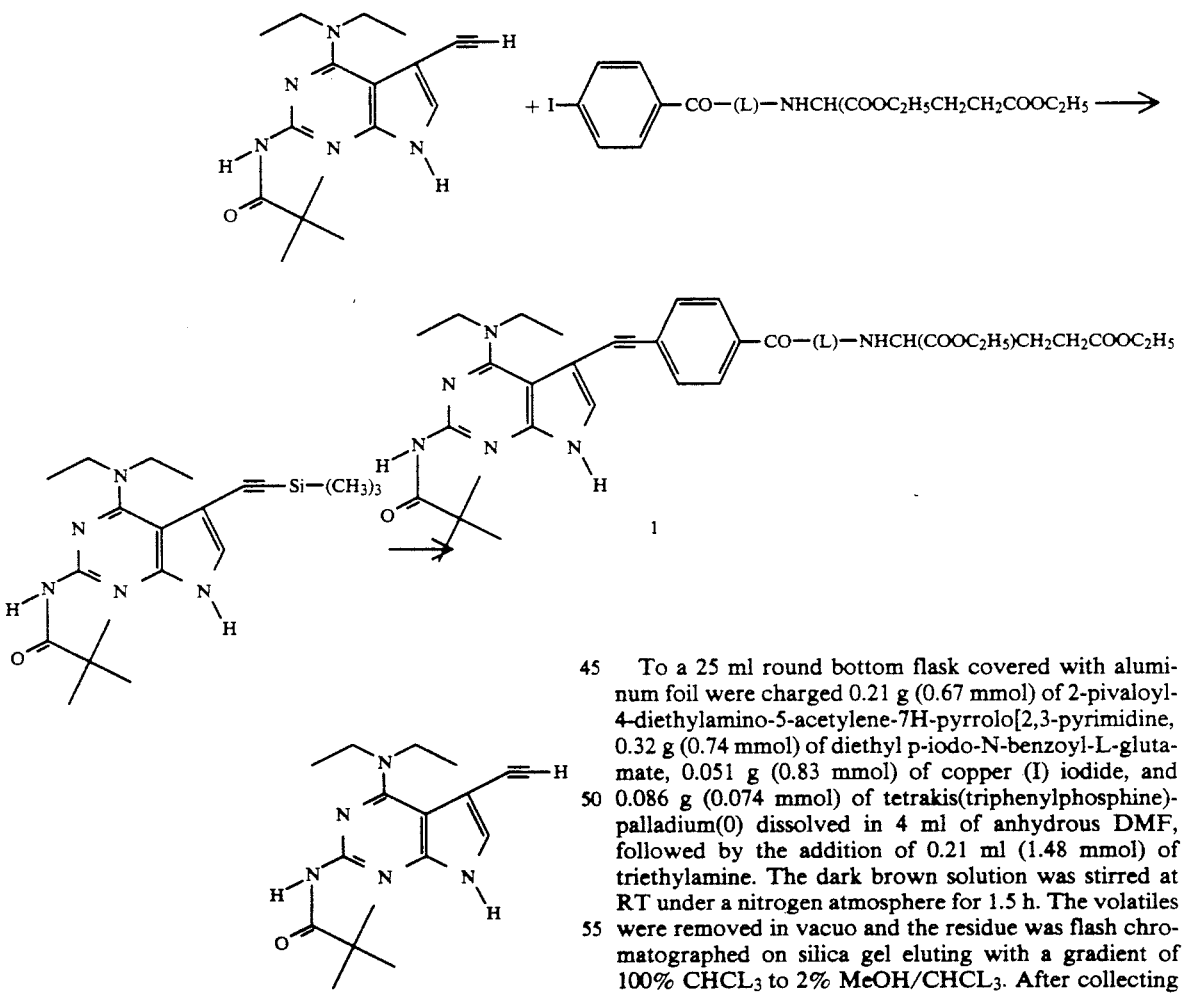

To a 15 ml round bottom flask were charged 0.10 g (0.26 mmol) of 2-pivaloyl-4-diethylamino-5-(trimethylsilyl)acetylene-7H-pyrrolo[2,3-d]pyrimidine, and 0.39 ml (0.39 mmol) of tetrabutylammonium fluoride dissolved in 2 ml of anhydrous THF. The reaction was stirred at RT under a nitrogen atmosphere for 30 min. The reaction was then quenched by pouring it into 50 ml CHCl$_3$ and washing with water. The organic layer was separated away, dried over Na$_2$SO$_4$, and removed in vacuo. This residue was then flash chromatographed eluting with 2% MeOH/CHCL$_3$. After collecting the correct fractions, the solvents were removed in vacuo to give 0.079 g (97%) of 2-pivaloyl-4-diethylamino-5-acetylene-7H-pyrrolo[2,3-pyrimidine as a tan solid.

R$_f$=0.32 (5% MeOH/CHCL$_3$)
m.p.=71°–74° C. (dec)
Mass (FAB)=314

IR (KBr, cm$^{-1}$)=721, 789, 806, 834, 946, 1033, 1091, 1162, 1206, 1279, 1300, 1358, 1370, 1428, 1536, 1571, 1707, 2102, 2969, 3195, 3454

UV (EtOH) $^1$max =295, 237, 206 (e=15267, 26168, 20274)

$^1$H NMR (300 MHz, DMSO$_{d6}$) d 1.11–1.22 (m, 15H), 3.80 (q, J=6.8 Hz, 4H), 4.01 (s, 1H), 7.47 (s, 1H), 9.02 (s, 1H), 11.81 (s, 1H)

D. Preparation of diethyl N-[2-pivaloyl-4-diethylamino-[[pyrrolo[2,3-d]pyrimidin-5-yl]ethynyl]benzoyl]-L-glutamate To a 25 ml round bottom flask covered with aluminum foil were charged 0.21 g (0.67 mmol) of 2-pivaloyl-4-diethylamino-5-acetylene-7H-pyrrolo[2,3-pyrimidine, 0.32 g (0.74 mmol) of diethyl p-iodo-N-benzoyl-L-glutamate, 0.051 g (0.83 mmol) of copper (I) iodide, and 0.086 g (0.074 mmol) of tetrakis(triphenylphosphine)palladium(0) dissolved in 4 ml of anhydrous DMF, followed by the addition of 0.21 ml (1.48 mmol) of triethylamine. The dark brown solution was stirred at RT under a nitrogen atmosphere for 1.5 h. The volatiles were removed in vacuo and the residue was flash chromatographed on silica gel eluting with a gradient of 100% CHCL$_3$ to 2% MeOH/CHCL$_3$. After collecting the correct fractions, the solvents were removed in vacuo, and the solid was triturated in 15 ml of ether to give 0.18 g (45%) of 1 as an off-white solid.

R$_f$=0.32 (5% MeOH/CHCL$_3$)
m.p.=171°–174° C. (dec)
Mass (FAB)=619

IR (KBr, cm$^{-1}$)=1092, 1174, 1213, 1261, 1303, 1392, 1426, 1494, 1534, 1571, 1604, 1650, 1669, 1738, 2202, 2933, 2977

UV (EtOH) $^1$max =340, 291, 272, 245, 202 (e=18314, 21270, 247273, 34009, 38018)

$^1$H NMR (300 MHz, DMSO$_{d6}$) d 1.12–1.21 (m, 21H), 1.96–2.10 (m, 2H), 2.40–2.43 (m, 2H), 3.90 (q, J=6.4 Hz, 4H), 3.96–4.12 (m, 4H), 4.40–4.45 (m, 1H), 7.54 (d, J=8.0 Hz, 2H), 7.66 (s, 1H), 7.78 (d, J=8.1 Hz, 2H), 8.78 (d, J=7.3 Hz, 1H), 9.12 (s, 1H), 12.01 (s, 1H)

E. Preparation of diethyl N-[2-pivaloyl-4-diethylamino-[[pyrrolo[2,3-d]pyrimidin-5-yl]ethyl]-benozyl]-L-glutamate

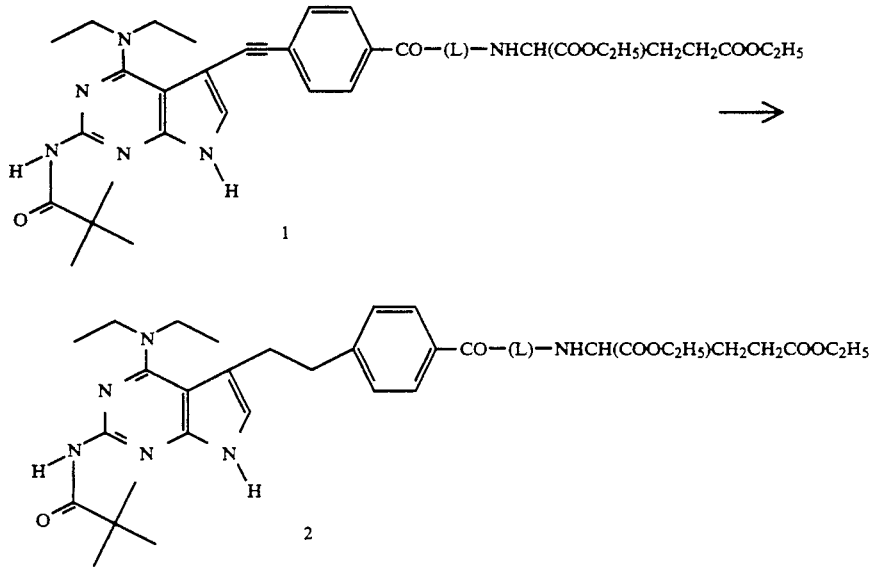

To a Parr hydrogenation bottle was charged 0.17 g (0.27 mmol) of 1 dissolved in 10 ml of absolute ethanol and 2 ml of dichloromethane, followed by the addition of 0.25 g of 10% pd/C catalyst. This mixture was then washing thoroughly the catalyst, the filtrate was removed in vacuo. The crude residue was then flash chromatographed on silic gel eluting with 2% MeOH/CHCl$_3$. After collecting the correct fractions, the solvents were removed in vacuo to give 0.13 g (76%) of 2 as an off-white solid.

R$_f$=0.25 (5% MeOH/CHCl$_3$)
m.p.=68°–71° C.

Mass (FAB)=623

IR (KBr, cm$^{-1}$)=763, 792, 1020, 1083, 1167, 1191, 1260, 1299, 1377, 1421, 1468, 1506, 1537, 1574, 1612, 1648, 1704, 1737, 2872, 2935, 2975, 3292, 3455

UV (EtOH) $^l$max=296, 243, 203 (e, 11472, 43662, 43729)

Anal. Calcd for C$_{33}$H$_{46}$N$_6$O$_6$: C, 63.65; H, 7.44; N, 13.4. Found: C, 63.45; H, 7.52; N, 13.46.

$^1$H NMR (300 MHz, DMSO$_{d6}$) d 1.07–1.19 (m, 21H), 1.90–2.10 (m, 2H), 2.40 (t, J=7.5 Hz, 2H, 3.30 (s, 4H), 3.52 (q, J=6.8 Hz, 4H), 3.98–4.11 (m, 4H), .961 (s, 1H), 7.26 (d, J=8.2 Hz, 2H), 7.74 (d, J=8.1 Hz, 2H), 8.60 (d, J=7.4 Hz, 1H), 9.15 (s, 1H), 11.26 (s, 1H)

F. Preparation of N-[2-amino-4-diethylamino-[[pyrrolo[2,3-d]pyrimidin-5-yl]ethyl]benzoyl]-L-glutamic acid

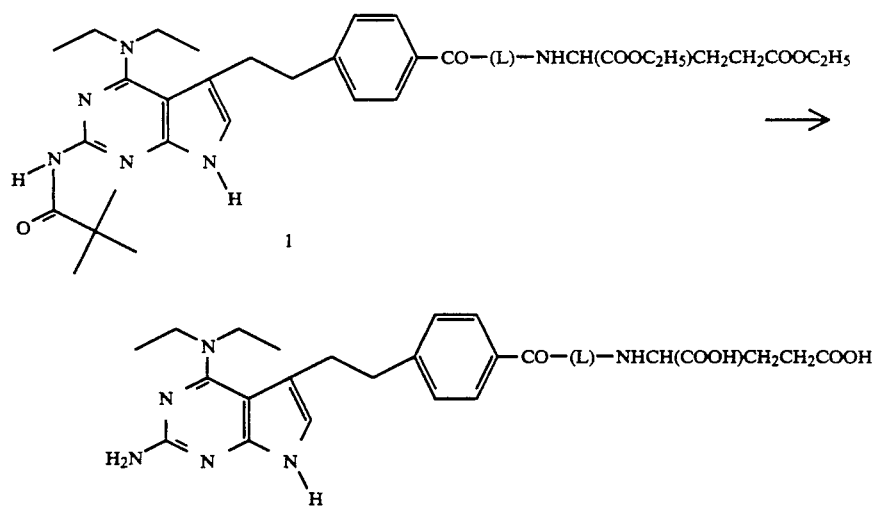

To a 15 ml round bottom flask was charged 0.065 g (0.10 mmol) of 1 suspended in 3 ml of 1 N NaOH. The reaction was stirred at RT for 7.5 days. The yellow solution was acidified with 1 N HCl, and the precipitate was cooled down in an ice bathm, filtered, washed with water, and dried in a vacuum oven at 70° C. to give 0.021 g (42%) of 2 as a pale yellow solid.

R/0.09 (50% MeOH/CHCl₃)
m.p.=160°-163° C. (dec)
Mass (FAB)=483
IR (KBr, cm⁻¹)=724, 766, 851, 930, 990, 1020, 1079, 1098, 1206, 1298, 1354, 1401, 1436, 1503, 1533, 1567, 1612, 1656, 2873, 2935, 3209, 3331
UV (EtOH) ¹max=306, 235, 202 (e=5778, 25046, 26120)
¹H NMR (300 MHz, DMSO$_{d6}$) d 0.94–1.12 (m, 6H), 1.90–2.07 (m, 2H), 2.30–2.34 (m, 2H), 3.16–3.49 (m, 8H), 4.35–4.36 (m, 1H, 5.59 (s, 2H, 6.56 (s, 1H), 7.24 (d, J=7.8 Hz, 2H), 7.76 (d, J=7.8 Hz, 2H), 8,.48 (d, J=7.6 Hz, 1H), 10.58 (s, 1H), 12.15 (br s, 1H)

EXAMPLE 7

A. Preparation of 2-pivaloyl-4-ethylthio-5-acetylenepyrido[2,3-d]pyrimidine

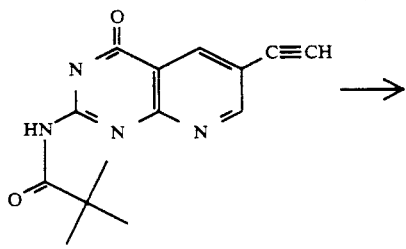

→

1.0 Gram of 2-pivaloyl-4-oxo-pyrido(2,3-d)pyrimidine was reacted with 10 ml of POCl3 in the presence of 1 ml of N,N-diethylaniline while heating to 100° C. for 20 minutes under a nitrogen atmosphere. Afterward, the volatiles were removed in vacuo. The residue was dissolved in 25 ml of methylene chloride and reacted with 1 ml of ethanethiol for 45 minutes. Afterward, any volatiles present were again removed in vacuo. The residue was dissolved in methylene chloride and washed twice with water. The resulting organic layer was then dried with Na₂SO₄. after which the solvent was removed in vacuo.

The crude residue was then flash chromatographed on silica gel eluting with 25 % EtoAl/MeCl2. Agter collecting the correct fractions, the solvents were removed in vacuo to give 0.262 (22%) of a yellow solid for the two steps.

mp 120°-123° C.
UV (EtOH)- 362, 282, 244, 205
Mass (FAB)=314
R/=0.48 (1:1 Etoac/MeCl₂)
¹H NMR (300 MHz, CDC13) d 1.38 (2, 9H), 1.51 (t, J=7.4Hz, 3H), 3.54(9,J=7.4 Hz, 2H) 8.28 (s, 1H0, 8.44 (d,J =2.2 Hz, 1H) 9.09 (d, J=2.2 H2, 1H)
IR (KBr, cm⁻¹)=666, 763, 812, 847, 893, 923, 978, 1020, 1137, 1198, 1224, 1346, 1376, 1407, 1551, 1707, 1743, 2967, 3236

B. Preparation of diethyl N-[2-pivaloyl-4-ethylthio[[-pyrido[2,3-d]pyrimidin-5-yl]ethynyl]benzoyl]-L-glutamate

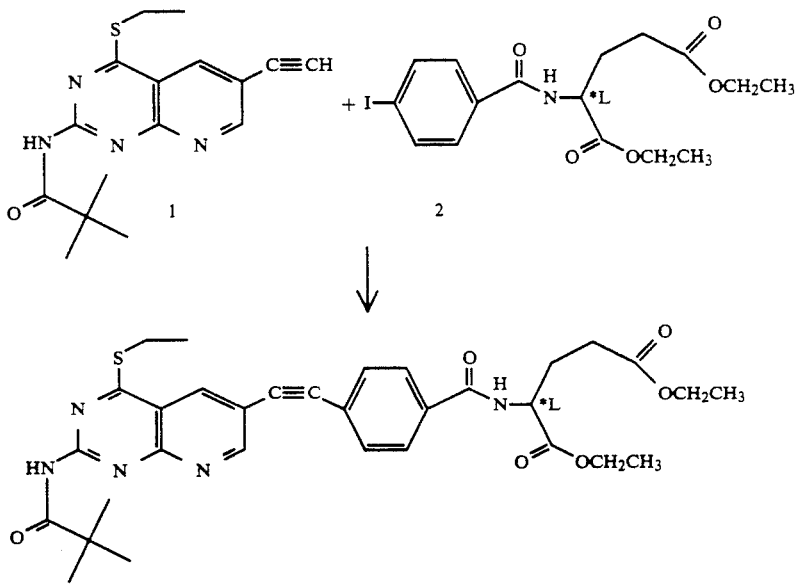

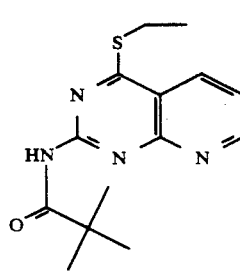

0.009 Grams of PdCl₂ and 0.028 grams of triphenylphosphine were combined with 3 ml of accetonitrile for 30 minutes. After which, 0.30 grams of 1 (above), 0.45 grams of 2 (above), 0.005 grams of CuI, 7 ml of acetonitrile, and 0.31 ml of triethylamine were added to the reaction mixture. The mixture was heated to 80° C. for 20 minutes. The product was dissolved in excess methylene chloride and washed with water. The organic layer was then dried with Na₂SO₄ and the solvent removed in vacuo.

The crude residue was then flash chromatographed on silicagel eluting with 25% EtOAc/MeC12. After collecting the correct fraction, the solvents were removed in vacuo to give 0.21 g (36%) of a yellow solid.

$R_f$=0.42 (1:1 EtOAc/MeC12)
UV (EtOH)=373, 326, 306, 252
Mass (FAB)=619
mp=97°-100 ° C.

¹H NMR (300, CDC13) d 1.26 (t, J=7.1 Hz, 3H), 1.34 (t, J=7.1 Hz, 3H), 1.50 (s, 9H), 1.57 (t, J=6.9 Hz, 3H), 2.16-2.20 (m, 1H), 2.23-2.36 (M,1H), 2.48-2.59 (m,2H), (m,2H), 4.14 (9, J=7.2Hz, 2H), 4.28 (9, J - 8.2 Hz, 2H), 7.90 (d, J=8.2 Hz, 2H0, 8.53 (s,1H) 9.16 (S,1H)

IR (KBr, Cm⁻¹)=662, 769, 792, 856, 905, 979, 1020, 1132, 1202, 1261, 1304, 1332, 1372, 1400, 1496, 1552, 1597, 1660, 1735, 2976, 3378

C. Preparation of diethyl N-[2-pivaloyl-tetrahydropyrido[2,3-d]pyrimidin-5-yl]ethyl]benzoyl]-L-glutamate correct fractions, the solvents were removed in vacuo to give 0.025 g (27%) of a yellow solid.

$R_f$=0.27 15% MeOH/CHCl3)
UV (EtOH)=298, 225, 202
Mass (FAB)=619
mp=168°-170 ° C.

¹H NMR (300,CDC13) d 1.21 (t,J=3.4Hz,3H), 1.24-1.39 (m,12H), 1.69-1.75 (m,2H), 1.80-2.14(m,1H) 2.16-2.19 (m,1H,
2.30-2.50(m,4H), 2.74-2.82 (m,2H), 3.10-3.25(m1H), 3.46-3.51(m,2H), 4.15(9,J=6.9Hz,2H), 4.26(9,J=7.0 Hz, 2H0, 4.75-4.85(m,1H0, 5.40 (s,1H), 7.00 (d,J=7.1Hz, 1H0, 7.3old, J=10.0H2,2H0, 7.75 (s,1H0, 7.80(d,J+10.2Hz)

IRCKBr,CM-1)=542, 613, 785, 857, 927, 1022, 1097, 155, 1207, 1260, 1300, 1373, 1421, 1503, 1542, 1574, 1613, 658, 1736, 2931, 3338

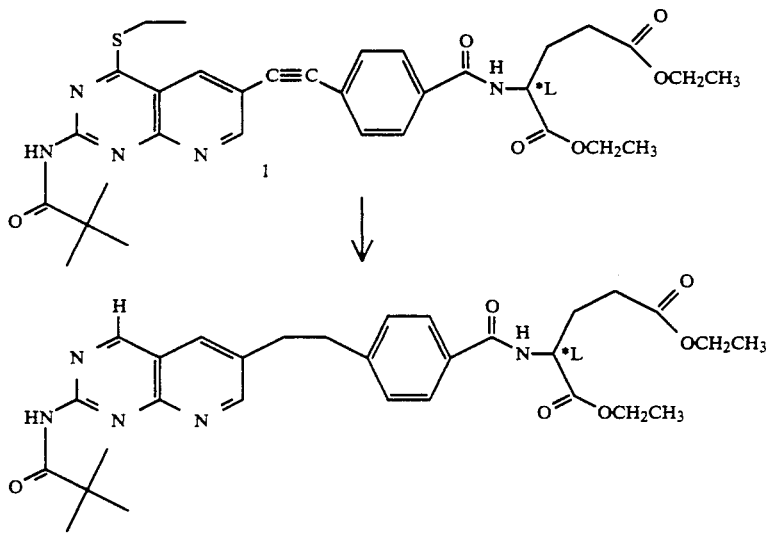

0.10 Grams Of 1, above, was dissolved in 3 ml of methylene chloride and diluted with 15 ml of ethanol. The resulting solution was subjected to hydrogenation at 60 psi with a Raney-Nickel catalyst. The reaction was carried at room temperature for 2 hours and at 60° C. for an additional 3 hours. The solvent was removed from product in vacuo.

The cruse residue was then flash chromotographed eluting with 5% MeOH/CHCL3. After collecting the D. Preparation of N-[2-amino-[tetrahydropyrido[2,3-d]pyrimidin-5-yl]ethyl]benzoyl]-L-glutamic acid

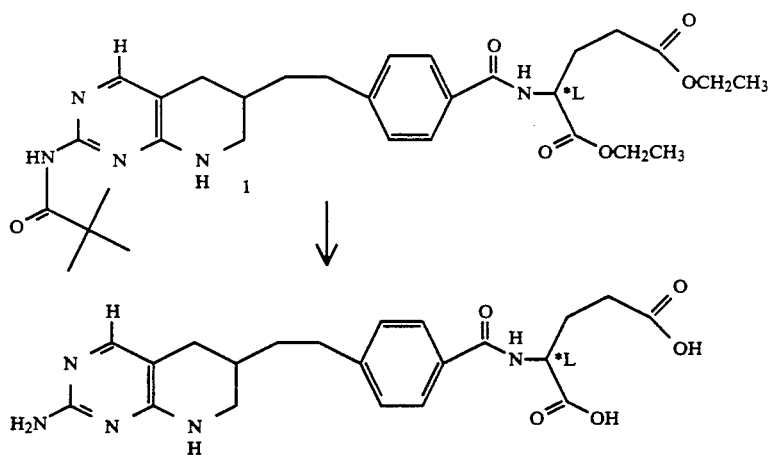

0.039 Grams of 1 above,in 1 ml of methanol, was reacted with 1.5 ml of 1 N sodium hydroxide. The reaction mixture was stirred for 3½ days after which the solution was acidified to a pH of 6 with 5 N HCl. The yellow precipitate thusly formed was filtered, washed with H2O, and dried in a vacuum oven at 60° C.

$R_f = 0.05$ (50% MeOH/CHC3)
mp = 250°–253° C.
Mass (FAB) = 428
UV (EtOH) = 230, 202
$^1$H NMR (300, DMsOd6) d 1.57 (t,J=7.3, 3H), 1.62–1.67 (m,2H), 1.92–2.01(m,2H), 2.18–2.21 (m,2H), 2.30 (t,J=7.0Hz,2H) 2.48–2.71 (m,2H), 2.90–3.10(m,2H), 4.31–4.34 (m,1H) 6.31 (s,2H), 7.29(d,J=8.0Hz, 2H), 7.36 (d,J=1.2Hz, 1H), 7.41 (d,J=2.5Hz, 1H), 7.77(d,J=8.0Hz,2H), 8.39 (d,J=7.2Hz,1H)
IR(KBr,cm−1)=583, 768, 1100, 1379, 1451, 1502, 1537, 1585, 1662, 2929, 3333

We claim:

1. A compound of the formula:

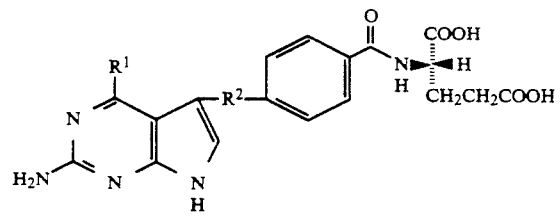

wherein
$R^1$ is hydrogen, chloro, $C_1$–$C_4$ alkylthio, $C_1$–$C_4$ alkoxy, $C_1$–$C_4$ alkylamino, or di($C_1$–$C_4$) alkylamino; and
$R^2$ is $C_2$–$C_3$ alkyl; or a pharmaceutically acceptable salt thereof.

2. The compound of claim 1 which is N-[2-amino-4-chloro-[[pyrrolo[2,3-d]-pyrimidin-5-yl]ethyl]benzoyl]-L-glutamic acid or a pharmaceutically acceptable salt thereof.

3. The compound of claim 1 which is N-[2-amino-[[pyrrolo[2,3-d]-pyrimidin-5-yl]-ethyl]benzoyl]-L-glutamic acid or a pharmaceutically acceptable salt thereof.

4. The compound of claim 1 which is N-[2-amino-4-methoxy-[[pyrrolo[2,3-d]-pyrimidin-5-yl]-ethyl]benzoyl]-L-glutamic acid or a pharmaceutically acceptable salt thereof.

5. The compound of claim 1 which is N-[2-amino-4-diethylamino-[[pyrrolo[2,3-d]-pyrimidin-5-yl]-ethyl]benzoyl]-L-glutamic acid or a pharmaceutically acceptable salt thereof.

6. A compound of the formula:

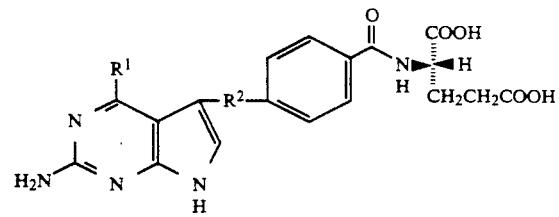

wherein:
$R^1$ is hydrogen, chloro, $C_1$–$C_4$ alkylthio, $C_1$–$C_4$ alkoxy, $C_1$–$C_4$ alkylamine, or di($C_1$–$C_4$) alkylamino; and
$R^2$ is $C_2$–$C_3$ alkyl; or a pharmaceutically acceptable salt thereof.

7. The compound of claim 6 which is N-[2-aminodihydro-[pyrrolo[2,3-d]-pyrimidin-5-yl]-ethyl]benzoyl]-L-glutamic acid or a pharmaceutically acceptable salt thereof.

8. A compound of the formula:

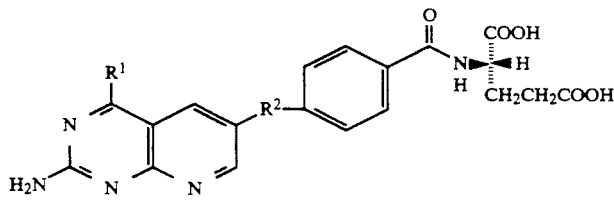

wherein:
$R^1$ is hydrogen, chloro, $C_1$–$C_4$ alkylthio, $C_1$–$C_4$ alkoxy, $C_1$–$C_4$ alkylamine, or di($C_1$–$C_4$) alkylamino; and
$R^2$ is $C_2$–$C_3$ alkyl; or a pharmaceutically acceptable salt thereof.

9. A compound of the formula:

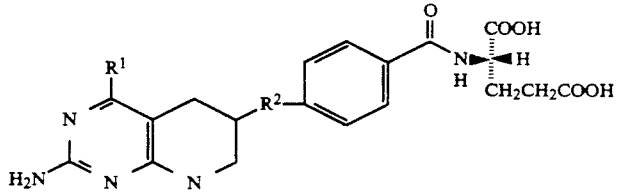

wherein:
$R^1$ is hydrogen, chloro, $C_1$–$C_4$ alkylthio, $C_1$–$C_4$ alkoxy, $C_1$–$C_4$ alkylamine, or di($C_1$–$C_4$) alkylamino; and
$R^2$ is $C_2$–$C_3$ alkyl; or a pharmaceutically acceptable salt thereof.

10. The compound of claim 9 which is N-[2-amino-[tetrahydropyrido[2,3-d]pyrimidine-5-yl]ethyl]-benzoyl]-L-glutamic acid.

11. A method of treating susceptible neoplasms in a mammal in need of such treatment comprising administering a neoplasm growth inhibiting dose of a compound according to claim 1.

12. A method of treating susceptible neoplasms in a mammal in need of such treatment comprising administering a neoplasm growth inhibiting dose of a compound according to claim 6.

13. A method of treating susceptible neoplasms in a mammal in need of such treatment comprising administering a neoplasm growth inhibiting dose of a compound according to claim 8.

14. A method of treating susceptible neoplasm in a mammal in need of such treatment comprising administering a neoplasm growth inhibiting dose of a compound according to claim 9.

15. A pharmaceutical composition comprising a compound according to claim 1 in combination with a pharmaceutically acceptable carrier, diluent or excipient.

16. A pharmaceutical composition comprising a compound according to claim 6 in combination with a pharmaceutically acceptable carrier, diluent or excipient.

17. A pharmaceutical composition comprising a compound according to claim 8 in combination with a pharmaceutically acceptable carrier, diluent or excipient.

18. A pharmaceutical composition comprising a compound according to claim 9 in combination with a pharmaceutically acceptable carrier, diluent or excipient.

19. A compound of the formula

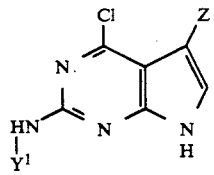

where
$Y^1$ is hydrogen or an amino protecting group;
Z is hydrogen, bromo or iodo; and pharmaceutically acceptable salts thereof.

20. A compound of the formula

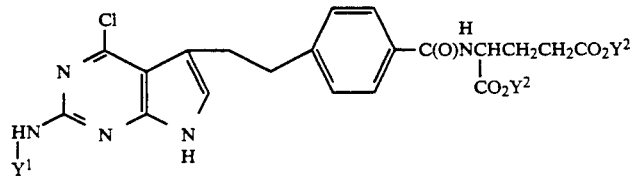

where:
$Y^1$ is an amino protecting group;
$Y^2$ is the same or different carboxy protecting pharmaceutically acceptable salts thereof.

* * * * *

UNITED STATES PATENT AND TRADEMARK OFFICE
CERTIFICATE OF CORRECTION

PATENT NO.    :   5,196,424

DATED         :   March 23, 1993

INVENTOR(S)   :   Lynn S. Gossett, et al.

It is certified that an error appears in the above-identified patent and that said Letters Patent is hereby corrected as shown below:

In column 10, line 46, "R2" should read as -- $R^2$ --.
In column 19, line 62, "d]pyrimidine as a" should read as -- d]pyrimidine as a tan solid --.
In column 20, line 63, "(s,9H(, 197-213" should read as -- (s,9H), 1.97-2.13 --.
In column 22, line 68, "38829," should read as -- 38829, 34937) --.
In column 24, line 45, "3.14-3 22" should read as -- 3.14-3.22 --.
In column 26, line 32, "$C_{20}$" should read as -- $C_{29}$ --.
In column 31, line 35, "C11H13N4OCl" should read as -- $C_{11}H_{13}N_4OCl$ --.
In column 36, line 24, "232," should read as -- 1232, --.
In column 36, line 25, "961," should read as -- 2961, --.
In column 37, line 2, "6,95" should read as -- 695 --.
In column 37, line 8, "7.62" should read as -- 7.52 --.
In column 40, line 8, "13.4." should read as -- 13.49.--.
In column 40, line 35, ".961" should read as -- 6.91 --.
In column 41, line 9, "1612, 1656, 2873, 2935, 3209, 3331" should read as -- 1612, 1656, 2873, 2935, 2975, 3209, 3331 --.
In column 41, line 15, "8,.48" should read as -- 8.48 --.
In column 42, line 11, "$Na_2SO_4$." should read as -- $Na_2SO_{4,}$ --.
In column 42, line 14, "Agter" should read as -- After --.
In column 43, lines 9 and 10, "(m,2H), (m,2H)," should read -- (m,2H), 3.70-3.77 (m,2H), --.
In column 44, line 16, "155," should read as -- 1155, --.
In column 44, line 17, "658," should read as -- 1658, --.
In column 45, line 1, "(50% MeOH/CHC3)" should read as -- (50% MeOH/CHCl3) --.

UNITED STATES PATENT AND TRADEMARK OFFICE
CERTIFICATE OF CORRECTION

PATENT NO. : 5,196,424
DATED : March 23, 1993
INVENTOR(S) : Lynn S. Gossett, et al.

It is certified that error appears in the above-indentified patent and that said Letters Patent is hereby corrected as shown below:

Column 46, line 54, "alkylamine," should read as --alkylamino, --.

Signed and Sealed this

Twenty-sixth Day of April, 1994

Attest:

BRUCE LEHMAN

Attesting Officer

Commissioner of Patents and Trademarks